(12) United States Patent
Sunahara et al.

(10) Patent No.: US 8,501,692 B2
(45) Date of Patent: Aug. 6, 2013

(54) COMPOSITIONS AND METHODS FOR ALTERING COCAINE ESTERASE ACTIVITY

(75) Inventors: Roger K. Sunahara, Ann Arbor, MI (US); John J. G. Tesmer, Ann Arbor, MI (US); Diwahar Narasimhan, Ypsilanti, MI (US); James H. Woods, Ann Arbor, MI (US); Mark R. Nance, Ann Arbor, MI (US); Elin Edwald, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/515,511

(22) PCT Filed: Dec. 14, 2010

(86) PCT No.: PCT/US2010/060278
§ 371 (c)(1),
(2), (4) Date: Nov. 2, 2012

(87) PCT Pub. No.: WO2011/081928
PCT Pub. Date: Jul. 7, 2011

(65) Prior Publication Data
US 2013/0039900 A1 Feb. 14, 2013

Related U.S. Application Data

(60) Provisional application No. 61/286,053, filed on Dec. 14, 2009.

(51) Int. Cl.
*C07K 1/00* (2006.01)
*A61K 38/00* (2006.01)
*C07H 21/04* (2006.01)

(52) U.S. Cl.
USPC ......... 514/12.1; 514/18.2; 536/23.2; 530/350

(58) Field of Classification Search
USPC .......................... 530/350; 536/23.1; 514/12.1
See application file for complete search history.

(56) References Cited

FOREIGN PATENT DOCUMENTS
WO 2008008358 * 1/2008
WO 2008008358 A2 1/2008

OTHER PUBLICATIONS

Baird et al., "Natural and artificial enzymes against cocaine. I. Monoclonal antibody 15A10 and the reinforcing effects of cocaine in rats." J Pharmacol Exp Ther. Dec. 2000;295(3):1127-34.
Benowitz NL, "Clinical pharmacology and toxicology of cocaine." Pharmacol Toxicol. Jan. 1993;72(1):3-12.
Bresler et al., "Gene cloning and nucleotide sequencing and properties of a cocaine esterase from Rhodococcus sp. strain MB1." Appl Environ Microbiol. Mar. 2000;66(3):904-8.
Browne et al., "The influence of plasma butyrylcholinesterase concentration on the in vitro hydrolysis of cocaine in human plasma." Biopharm Drug Dispos. Jul. 1998;19(5):309-14.
Carmona et al., "Plasma butyrylcholinesterase activity and cocaine half-life differ significantly in rhesus and squirrel monkeys." Life Sci. 1996; 59(11):939-43.
Carrera et al., "A second-generation vaccine protects against the psychoactive effects of cocaine." Proc Natl Acad Sci U S A. Feb. 13, 2001;98(4):1988-92.
Carrera et al., "Treating cocaine addiction with viruses." Proc Natl Acad Sci U S A. Jul. 13, 2004;101(28):10416-21.
Cooper et al., "Rapid and robust protection against cocaine-induced lethality in rats by the bacterial cocaine esterase." Mol Pharmacol. Dec. 2006;70(6):1885-91.
Crumb & Clarkson, "Characterization of cocaine-induced block of cardiac sodium channels." Biophys J. Mar. 1990;57(3):589-99.
Deng et al., "Anticocaine catalytic antibodies." J Immunol Methods. Nov. 1, 2002;269(1-2):299-310.
Gao et al., "Gene transfer of cocaine hydrolase suppresses cardiovascular responses to cocaine in rats." Mol Pharmacol. Jan. 2005;67(1):204-11.
Gao et al., "Thermostable variants of cocaine esterase for long-time protection against cocaine toxicity." Mol Pharmacol. Feb. 2009;75(2):318-23.
Gorelick & Gardner, "Agents in development for the management of cocaine abuse." Drugs. 2004; 64 (14):1547-73.
Gorelick, "Enhancing cocaine metabolism with butyrylcholinesterase as a treatment strategy." Drug Alcohol Depend. Dec. 15, 1997;48(3):159-65.
Johanson & Fischman, "The pharmacology of cocaine related to its abuse." Pharmacol Rev. Mar. 1989; 41 (1):3-52.
Kantak, "Vaccines against drugs of abuse: a viable treatment option?" Drugs. 2003; 63(4):341-52.
Ko et al, "Cocaine esterase: interactions with cocaine and immune responses in mice." J Pharmacol Exp Ther. Feb. 2007;320(2):926-33.
Liu et al., "Fundamental reaction mechanism and free energy profile for (-)-cocaine hydrolysis catalyzed by cocaine esterase." J Am Chem Soc. Aug. 26, 2009;131(33):11964-75.
Lynch et al., "Cocaine detoxification by human plasma butyrylcholinesterase." Toxicol Appl Pharmacol. Aug. 1997;145(2):363-71.
Mattes, "Therapeutic use of butyrylcholinesterase for cocaine intoxication." Toxicol Appl Pharmacol. Aug. 1997;145 (2):372-80.
Mckenzie et al., "Identification and characterization of single chain anti-cocaine catalytic antibodies." J Mol Biol. Jan. 19, 2007;365(3):722-31.

(Continued)

*Primary Examiner* — Maryam Monshipouri
(74) *Attorney, Agent, or Firm* — Casimir Jones SC

(57) ABSTRACT

The present invention relates to compositions and methods for treating and preventing cocaine addiction. In particular, the present invention provides mutated cocaine esterase proteins for use in treating and preventing cocaine addiction.

21 Claims, 25 Drawing Sheets

OTHER PUBLICATIONS

Meijler et al., "Fluorescent cocaine probes: a tool for the selection and engineering of therapeutic antibodies." J Am Chem Soc. Mar. 2, 2005;127(8):2477-84.

Mets et al, "A catalytic antibody against cocaine prevents cocaine's reinforcing and toxic effects in rats." Proc Natl Acad Sci U S A. Aug. 18, 1998;95(17):10176-81.

Narasimhan et al., "Structural analysis of thermostabilizing mutations of cocaine esterase." Protein Eng Des Sel. Jul. 2010;23(7):537-47.

Rogers et al, "Toward cocaine esterase therapeutics." J Am Chem Soc. Jul. 20, 2005;127(28):10016-7.

Sowdhamini et al., "Stereochemical modeling of disulfide bridges. Criteria for introduction into proteins by site-directed mutagenesis." Protein Eng. Nov. 1989;3(2):95-103.

Turner et al., "Biochemical characterization and structural analysis of a highly proficient cocaine esterase." Biochemistry. Oct. 15, 2002;41(41):12297-307.

Uhl et al., "Cocaine, reward, movement and monoamine transporters." Mol Psychiatry. 2002; 7(1):21-6.

* cited by examiner

Figure 12

CocE-wt (SEQ ID NO:1)
MVDGNYSVASNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSALIGTGLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNADRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKR

G4C/S10C-H6 (SEQ ID NO:2)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSALIGTGLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNADRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKRKLAAALEHHHHHH.

G4C/S10C/A295C-H6 (SEQ ID NO:3)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSALIGTGLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNcDRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKRKLAAALEHHHHHH

G4C/S10C/T172R/G173Q-H6 (SEQ ID NO:4)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSALIGrqLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNADRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI

Figure 12 (CONT)

VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKRKLAAALEHHHHHH

G4C/S10C/L169K/G173Q-H6 (SEQ ID NO:5)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSAkIGTqLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNADRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKRKLAAALEHHHHHH.

G4C/S10C (tagless) (SEQ ID NO:6)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSALIGTGLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNADRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKR.

G4C/S10C/A295C (tagless) (SEQ ID NO:7)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSALIGTGLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNcDRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKR G4C/S10C/T172R/G173Q (tagless) (SEQ ID NO:8)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSALIGrqLITSRSDARPEDAADFVQLAAILNDVAGAASVTPLAEQPLLGRLIPWVIDQVVDHPDNDESWQSISL

Figure 12 (CONT)

```
FERLGGLATPALITAGWYDGFVGESLRTFVAVKDNADARLVVGPWSHSNLTGRNADRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKR

G4C/S10C/L169K/G173Q (tagless) (SEQ ID NO:9)
MVDcNYSVAcNVMVPMRDGVRLAVDLYRPDADGPVPVLLVRNPYDKFDVFAWSTQSTNWLEFVRDGYAVVIQDTRGLFAS
EGEFVPHVDDEADAEDTLSWILEQAWCDGNVGMFGVSYLGVTQWQAAVSGVGGLKAIAPSMASADLYRAPWYGPGGALSV
EALLGWSAkIGTqLITSRSDARPEDAADFVQLAAILNDVAGAASVTPLAEQPLLGRLIPWVIDQVVDHPDNDESWQSISL
FERLGGLATPALITAGWYDGFVGESLRTFVAVKDNADARLVVGPWSHSNLTGRNADRKFGIAATYPIQEATTMHKAFFDR
HLRGETDALAGVPKVRLFVMGIDEWRDETDWPLPDTAYTPFYLGGSGAANTSTGGGTLSTSISGTESADTYLYDPADPVP
SLGGTLLFHNGDNGPADQRPIHDRDDVLCYSTEVLTDPVEVTGTVSARLFVSSSAVDTDFTAKLVDVFPDGRAIALCDGI
VRMRYRETLVNPTLIEAGEIYEVAIDMLATSNVFLPGHRIMVQVSSSNFPKYDRNSNTGGVIAREQLEEMCTAVNRIHRG
PEHPSHIVLPIIKR

G4C/S10C/T172R/G173Q-A92C-H6

(CCRQ-A92C-H6) (SEQ ID NO:16)

MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD ECDAEDTLSW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLCY STEVLTDPVE VTGTVSARLF VSSSAVDTDF TAKLVDVFPD GRAIALCDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKRKLAAAL EHHHHHH

G4C/S10C/T172R/G173Q-S99C-H6

CCRQ-S99C-H6)(SEQ ID NO:17)

MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD EADAEDTLCW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLCY STEVLTDPVE VTGTVSARLF VSSSAVDTDF TAKLVDVFPD GRAIALCDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKRKLAAAL EHHHHHH
```

Figure 12 (CONT)

G4C/S10C/T172R/G173Q-A92C (CCRQ-A92C) (SEQ ID NO:18)

MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD ECDAEDTLSW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLCY STEVLTDPVE VTGTVSARLF VSSSAVDTDF TAKLVDVFPD GRAIALCDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKR

G4C/S10C/T172R/G173Q-S99C (CCRQ-S99C)(SEQ ID NO:19)

MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD EADAEDTLCW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLCY STEVLTDPVE VTGTVSARLF VSSSAVDTDF TAKLVDVFPD GRAIALCDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKR

G4C/S10C/T172R/G173Q-C429S/C477S (CCRQ-C429S/C477S)(SEQ ID NO:20)

MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD EADAEDTLSW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLSY STEVLTDPVE VTGTVSARLF VSSSAVDTDF TAKLVDVFPD GRAIALSDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKR

G4C/S10C/T172R/G173Q-A92C/C429S/C477S (CCRQ-A92C/C429S/C477S)(SEQ ID NO:21)

MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD ECDAEDTLSW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLSY STEVLTDPVE VTGTVSARLF VSSSAVDTDF TAKLVDVFPD GRAIALSDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKR

Figure 12 (CONT)

G4C/S10C/T172R/G173Q-S99C/C429S/C477S (CCRQ-S99C/C429S/C477S) (SEQ ID NO:22)

```
MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD EADAEDTLCW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLSY STEVLTDPVE VTGTVSARLF VSSSAVDTDF TAKLVDVFPD GRAIALSDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKR
```

G4C/S10C/T172R/G173Q-C429S/C477S-H6

(CCRQ-C429S/C477S-H6) (SEQ ID NO:23)

```
MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD EADAEDTLSW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLSY STEVLTDPVE VTGTVSARLF VSSSAVDTDF TAKLVDVFPD GRAIALSDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKRKLAAAL EHHHHHH
```

G4C/S10C/T172R/G173Q-A92C/C429S/C477S-H6

(CCRQ-A92C/C429S/C477S-H6)(SEQ ID NO:24)

```
MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD ECDAEDTLSW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLSY STEVLTDPVE VTGTVSARLF VSSSAVDTDF TAKLVDVFPD GRAIALSDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKRKLAAAL EHHHHHH
```

(CCRQ-S99C/C429S/C477S-H6) (SEQ ID NO:25)

```
MVDGNYSVAS NVMVPMRDGV RLAVDLYRPD ADGPVPVLLV RNPYDKFDVF AWSTQSTNWL EFVRDGYAVV
IQDTRGLFAS EGEFVPHVDD EADAEDTLCW ILEQAWCDGN VGMFGVSYLG VTQWQAAVSG VGGLKAIAPS
MASADLYRAP WYGPGGALSV EALLGWSALI GTGLITSRSD ARPEDAADFV QLAAILNDVA GAASVTPLAE
QPLLGRLIPW VIDQVVDHPD NDESWQSISL FERLGGLATP ALITAGWYDG FVGESLRTFV AVKDNADARL
VVGPWSHSNL TGRNADRKFG IAATYPIQEA TTMHKAFFDR HLRGETDALA GVPKVRLFVM GIDEWRDETD
WPLPDTAYTP FYLGGSGAAN TSTGGGTLST SISGTESADT YLYDPADPVP SLGGTLLFHN GDNGPADQRP
IHDRDDVLSY STEVLTDPVE VTGTVSARLF VSSSAVDTDF TAKLVDVFPD GRAIALSDGI VRMRYRETLV
NPTLIEAGEI YEVAIDMLAT SNVFLPGHRI MVQVSSSNFP KYDRNSNTGG VIAREQLEEM CTAVNRIHRG
PEHPSHIVLP IIKRKLAAAL EHHHHHH
```

Figure 13

G4C/S10C (tagless) (SEQ ID NO:10)

```
   1 atggtggact gcaattacag tgttgcctgt aacgtgatgg ttccgatgcg tgatggggtg
  61 cgtctggcgg tcgacctgta ccgaccagat gctgatggac ctgttccggt cctgctggtt
 121 cgcaacccat acgacaagtt cgacgtgttc gcgtggtcga cgcagtcgac aaactggctt
 181 gagttcgtgc gtgatggcta tgccgtggtc attaagaca cgcgtggctt gttcgcatcg
 241 gaaggtgagt tcgtcccgca cgttgacgac gaagctgacg ccgaggatac gttgagctgg
 301 attctggaac aagcgtggtg cgacggcaat gtgggcatgt tcggcgtttc gtacttgggt
 361 gtgacccagt ggcaggccgc cgtatccggc gttggtgggc tgaaggcgat cgcgccgtcc
 421 atggcgtcgg cggacttgta ccgcgccccg tggtacggcc ctggtggtgc gctttcagtc
 481 gaggcgctgt tgggctggtc agctctcata ggtactgggc tcatcacgtc gaggtctgac
 541 gcccggcccg aagacgcagc cgacttcgtc caactcgcag caattctcaa tgacgtcgct
 601 ggcgcggcgt cggtcacgcc cctggccgag caaccgcttc tgggccgact gattccgtgg
 661 gtgatcgatc aggttgtcga tcaccccgac aacgatgaat catggcagtc cattagcttg
 721 tttgaacgac tcggcgggtt ggcaacaccg gccttgatca cggctgggtg gtacgacggg
 781 ttcgtcggcg aatcgttgcg cactttcgtt gcggtcaagg acaatgccga cgcacgtttg
 841 gttgtcggcc cttggagtca cagcaacctc actggtcgga atgcggaccg gaagttcggc
 901 attgccgcga cctacccgat tcaagaagcc accacgatgc acaaggcatt cttcgaccgg
 961 cacctccgcg cgagaccga tgcactcgca ggcgtcccca agtgcggct gttcgtaatg
1021 ggcatcgatg agtggcgtga cgaaacggac tggccactgc cggacacggc gtatacgccc
1081 ttctatcttg gaggtagcgg ggctgcgaat acctccacgg gtggtggaac actgtcgacg
1141 tcgatttccg gaactgaatc tgctgacacc tacctgtatg atccggccga tcccgtgcct
1201 tcgctcgggg ggacgctgct gttccacaac ggagacaacg acccgccga ccaacgtccc
1261 attcatgacc gggacgacgt gttgtgttac agcactgagg tattgaccga cccggtggaa
1321 gtaaccggca ccgtctccgc ccggctgttc gtgtcgtcat cagcggtgga cactgatttc
1381 accgccaaac ttgtcgacgt atttcccgac ggtcgcgcga tcgcgctgtg tgacgggatc
1441 gtgcggatgc ggtaccgcga cgttggtc aatccaacct tgatcgaagc gggcgaaatc
1501 tacgaggttg ctatcgacat gcttgcaacc tcgaatgtat tcctgccagg gcatcgcatc
1561 atggtccaag tatcaagtag caacttcccg aaatacgacc gcaattcgaa taccggcgga
1621 gtaatcgcac gggaacagct cgaagagatg tgcaccgccg tgaaccgcat tcaccgagga
1681 cctgagcatc ccagccacat tgtgctgccg attatcaagc gaTGA
```

G4C/S10C-H6 (SEQ ID NO:11)

```
   1 atggtggact gcaattacag tgttgcctgt aacgtgatgg ttccgatgcg tgatggggtg
  61 cgtctggcgg tcgacctgta ccgaccagat gctgatggac ctgttccggt cctgctggtt
 121 cgcaacccat acgacaagtt cgacgtgttc gcgtggtcga cgcagtcgac aaactggctt
 181 gagttcgtgc gtgatggcta tgccgtggtc attaagaca cgcgtggctt gttcgcatcg
 241 gaaggtgagt tcgtcccgca cgttgacgac gaagctgacg ccgaggatac gttgagctgg
 301 attctggaac aagcgtggtg cgacggcaat gtgggcatgt tcggcgtttc gtacttgggt
 361 gtgacccagt ggcaggccgc cgtatccggc gttggtgggc tgaaggcgat cgcgccgtcc
 421 atggcgtcgg cggacttgta ccgcgccccg tggtacggcc ctggtggtgc gctttcagtc
```

Figure 13 (CONT)

```
 481 gaggcgctgt tgggctggtc agctctcata ggtactgggc tcatcacgtc gaggtctgac
 541 gcccggcccg aagacgcagc cgacttcgtc caactcgcag caattctcaa tgacgtcgct
 601 ggcgcggcgt cggtcacgcc cctggccgag caaccgcttc tgggccgact gattccgtgg
 661 gtgatcgatc aggttgtcga tcaccccgac aacgatgaat catggcagtc cattagcttg
 721 tttgaacgac tcggcgggtt ggcaacaccg gccttgatca cggctgggtg gtacgacggg
 781 ttcgtcggcg aatcgttgcg cactttcgtt gcggtcaagg acaatgccga cgcacgtttg
 841 gttgtcggcc cttggagtca cagcaacctc actggtcgga atgcggaccg gaagttcggc
 901 attgccgcga cctacccgat tcaagaagcc accacgatgc acaaggcatt cttcgaccgg
 961 cacctccgcg gcgagaccga tgcactcgca ggcgtcccca agtgcggct gttcgtaatg
1021 ggcatcgatg agtggcgtga cgaaacggac tggccactgc cggacacggc gtatacgccc
1081 ttctatcttg gaggtagcgg ggctgcgaat acctccacgg gtggtggaac actgtcgacg
1141 tcgatttccg gaactgaatc tgctgacacc tacctgtatg atccggccga tcccgtgcct
1201 tcgctcgggg ggacgctgct gttccacaac ggagacaacg acccgccga ccaacgtccc
1261 attcatgacc gggacgacgt gttgtgttac agcactgagg tattgaccga cccggtggaa
1321 gtaaccggca ccgtctccgc ccggctgttc gtgtcgtcat cagcggtgga cactgatttc
1381 accgccaaac ttgtcgacgt atttcccgac ggtcgcgcga tcgcgctgtg tgacgggatc
1441 gtgcggatgc ggtaccgcga gacgttggtc aatccaacct tgatcgaagc gggcgaaatc
1501 tacgaggttg ctatcgacat gcttgcaacc tcgaatgtat tcctgccagg gcatcgcatc
1561 atggtccaag tatcaagtag caacttcccg aaatacgacc gcaattcgaa taccggcgga
1621 gtaatcgcac gggaacagct cgaagagatg tgcaccgccg tgaaccgcat tcaccgagga
1681 cctgagcatc ccagccacat tgtgctgccg attatcaagc gaAAGCTTGC GGCCGCACTC
1741 GAGCACCACC ACCACCACCA CTGA
```

G4C/S10C/T172R/G173Q (tagless) (SEQ ID NO:12)

```
   1 atggtggact gcaattacag tgttgcctgt aacgtgatgg ttccgatgcg tgatggggtg
  61 cgtctggcgg tcgacctgta ccgaccagat gctgatggac ctgttccggt cctgctggtt
 121 cgcaacccat acgacaagtt cgacgtgttc gcgtggtcga cgcagtcgac aaactggctt
 181 gagttcgtgc gtgatggcta tgccgtggtc attcaagaca cgcgtggctt gttcgcatcg
 241 gaaggtgagt tcgtcccgca cgttgacgac gaagctgacg ccgaggatac gttgagctgg
 301 attctggaac aagcgtggtg cgacggcaat gtgggcatgt tcggcgtttc gtacttgggt
 361 gtgacccagt ggcaggccgc cgtatccggc gttggtgggc tgaaggcgat cgcgccgtcc
 421 atggcgtcgg cggacttgta ccgcgccccg tggtacggcc tggtggtgc gcttcagtc
 481 gaggcgctgt tgggctggtc agctctcata ggtcgccagc tcatcacgtc gaggtctgac
 541 gcccggcccg aagacgcagc cgacttcgtc caactcgcag caattctcaa tgacgtcgct
 601 ggcgcggcgt cggtcacgcc cctggccgag caaccgcttc tgggccgact gattccgtgg
 661 gtgatcgatc aggttgtcga tcaccccgac aacgatgaat catggcagtc cattagcttg
 721 tttgaacgac tcggcgggtt ggcaacaccg gccttgatca cggctgggtg gtacgacggg
 781 ttcgtcggcg aatcgttgcg cactttcgtt gcggtcaagg acaatgccga cgcacgtttg
 841 gttgtcggcc cttggagtca cagcaacctc actggtcgga atgcggaccg gaagttcggc
 901 attgccgcga cctacccgat tcaagaagcc accacgatgc acaaggcatt cttcgaccgg
 961 cacctccgcg gcgagaccga tgcactcgca ggcgtcccca agtgcggct gttcgtaatg
```

Figure 13 (CONT)

```
1021 ggcatcgatg agtggcgtga cgaaacggac tggccactgc cggacacggc gtatacgccc
1081 ttctatcttg gaggtagcgg ggctgcgaat acctccacgg gtggtggaac actgtcgacg
1141 tcgatttccg gaactgaatc tgctgacacc tacctgtatg atccggccga tcccgtgcct
1201 tcgctcgggg ggacgctgct gttccacaac ggagacaacg acccgccga ccaacgtccc
1261 attcatgacc gggacgacgt gttgtgttac agcactgagg tattgaccga cccggtggaa
1321 gtaaccggca ccgtctccgc ccggctgttc gtgtcgtcat cagcggtgga cactgatttc
1381 accgccaaac ttgtcgacgt atttcccgac ggtcgcgcga tcgcgctgtg tgacgggatc
1441 gtgcggatgc ggtaccgcga cgttggtc aatccaacct tgatcgaagc gggcgaaatc
1501 tacgaggttg ctatcgacat gcttgcaacc tcgaatgtat tcctgccagg gcatcgcatc
1561 atggtccaag tatcaagtag caacttcccg aaatacgacc gcaattcgaa taccggcgga
1621 gtaatcgcac gggaacagct cgaagagatg tgcaccgccg tgaaccgcat tcaccgagga
1681 cctgagcatc ccagccacat tgtgctgccg attatcaagc gaTGA
```

G4C/S10C/T172R/G173Q-H6 (SEQ ID NO:13)

```
1 atggtggact gcaattacag tgttgcctgt aacgtgatgg ttccgatgcg tgatggggtg
61 cgtctggcgg tcgacctgta ccgaccagat gctgatggac ctgttccggt cctgctggtt
121 cgcaacccat acgacaagtt cgacgtgttc gcgtggtcga cgcagtcgac aaactggctt
181 gagttcgtgc gtgatggcta tgccgtggtc attcaagaca cgcgtggctt gttcgcatcg
241 gaaggtgagt tcgtcccgca cgttgacgac gaagctgacg ccgaggatac gttgagctgg
301 attctggaac aagcgtggtg cgacggcaat gtgggcatgt tcggcgtttc gtacttgggt
361 gtgacccagt ggcaggccgc cgtatccggc gttggtgggc tgaaggcgat cgcgccgtcc
421 atggcgtcgg cggacttgta ccgcgccccg tggtacggcc tggtggtgc gctttcagtc
481 gaggcgctgt tgggctggtc agctctcata ggtcgccagc tcatcacgtc gaggtctgac
541 gcccggcccg aagacgcagc cgacttcgtc caactcgcag caattctcaa tgacgtcgct
601 ggcgcggcgt cggtcacgcc cctggccgag caaccgcttc tgggccgact gattccgtgg
661 gtgatcgatc aggttgtcga tcaccccgac aacgatgaat catggcagtc cattagcttg
721 tttgaacgac tcggcgggtt ggcaacaccg gccttgatca cggctgggtg gtacgacggg
781 ttcgtcggcg aatcgttgcg cactttcgtt gcggtcaagg acaatgccga cgcacgtttg
841 gttgtcggcc cttggagtca cagcaacctc actggtcgga atgcggaccg gaagttcggc
901 attgccgcga cctacccgat tcaagaagcc accacgatgc acaaggcatt cttcgaccgg
961 cacctccgcg gcgagaccga tgcactcgca ggcgtcccca agtgcggct gttcgtaatg
1021 ggcatcgatg agtggcgtga cgaaacggac tggccactgc cggacacggc gtatacgccc
1081 ttctatcttg gaggtagcgg ggctgcgaat acctccacgg gtggtggaac actgtcgacg
1141 tcgatttccg gaactgaatc tgctgacacc tacctgtatg atccggccga tcccgtgcct
1201 tcgctcgggg ggacgctgct gttccacaac ggagacaacg acccgccga ccaacgtccc
1261 attcatgacc gggacgacgt gttgtgttac agcactgagg tattgaccga cccggtggaa
1321 gtaaccggca ccgtctccgc ccggctgttc gtgtcgtcat cagcggtgga cactgatttc
1381 accgccaaac ttgtcgacgt atttcccgac ggtcgcgcga tcgcgctgtg tgacgggatc
1441 gtgcggatgc ggtaccgcga cgttggtc aatccaacct tgatcgaagc gggcgaaatc
1501 tacgaggttg ctatcgacat gcttgcaacc tcgaatgtat tcctgccagg gcatcgcatc
1561 atggtccaag tatcaagtag caacttcccg aaatacgacc gcaattcgaa taccggcgga
```

Figure 13 (CONT)

```
1621 gtaatcgcac gggaacagct cgaagagatg tgcaccgccg tgaaccgcat tcaccgagga
1681 cctgagcatc ccagccacat tgtgctgccg attatcaagc gaAAGCTTGC GGCCGCACTC
1741 GAGCACCACC ACCACCACCA CTGA G4C/S10C/L169K/G173Q (tagless) (SEQ ID NO:14)
1    atggtggact gcaattacag tgttgcctgt aacgtgatgg ttccgatgcg tgatggggtg
61   cgtctggcgg tcgacctgta ccgaccagat gctgatggac ctgttccggt cctgctggtt
121  cgcaacccat acgacaagtt cgacgtgttc gcgtggtcga cgcagtcgac aaactggctt
181  gagttcgtgc gtgatggcta tgccgtggtc attcaagaca cgcgtggctt gttcgcatcg
241  gaaggtgagt cgtcccgca cgttgacgac gaagctgacg ccgaggatac gttgagctgg
301  attctggaac aagcgtggtg cgacggcaat gtgggcatgt cggcgtttc gtacttgggt
361  gtgacccagt ggcaggccgc cgtatccggc gttggtgggc tgaaggcgat cgcgccgtcc
421  atggcgtcgg cggacttgta ccgcgccccg tggtacggcc tggtggtgc gctttcagtc
481  gaggcgctgt tgggctggtc agctaagata ggtactcagc tcatcacgtc gaggtctgac
541  gcccggcccg aagacgcagc cgacttcgtc caactcgcag caattctcaa tgacgtcgct
601  ggcgcggcgt cggtcacgcc cctggccgag caaccgcttc tgggccgact gattccgtgg
661  gtgatcgatc aggttgtcga tcaccccgac aacgatgaat catggcagtc cattagcttg
721  tttgaacgac tcggcgggtt ggcaacaccg gccttgatca cggctgggtg gtacgacggg
781  ttcgtcggcg aatcgttgcg cactttcgtt gcggtcaagg acaatgccga cgcacgtttg
841  gttgtcggcc cttggagtca cagcaacctc actggtcgga atgcggaccg gaagttcggc
901  attgccgcga cctacccgat tcaagaagcc accacgatgc acaaggcatt cttcgaccgg
961  cacctccgcg gcgagaccga tgcactcgca ggcgtcccca agtgcggct gttcgtaatg
1021 ggcatcgatg agtggcgtga cgaaacggac tggccactgc cggacacggc gtatacgccc
1081 ttctatcttg gaggtagcgg ggctgcgaat acctccacgg tggtggaaac actgtcgacg
1141 tcgatttccg gaactgaatc tgctgacacc tacctgtatg atccggccga tcccgtgcct
1201 tcgctcgggg ggacgctgct gttccacaac ggagacaacg gacccgccga ccaacgtccc
1261 attcatgacc gggacgacgt gttgtgttac agcactgagg tattgaccga cccggtggaa
1321 gtaaccggca ccgtctccgc cggctgttc gtgtcgtcat cagcggtgga cactgatttc
1381 accgccaaac ttgtcgacgt atttcccgac ggtcgcgcga tcgcgctgtg tgacgggatc
1441 gtgcggatgc ggtaccgcga cgttggtc aatccaacct tgatcgaagc gggcgaaatc
1501 tacgaggttg ctatcgacat gcttgcaacc tcgaatgtat tcctgccagg gcatcgcatc
1561 atggtccaag tatcaagtag caacttcccg aaatacgacc gcaattcgaa taccggcgga
1621 gtaatcgcac gggaacagct cgaagagatg tgcaccgccg tgaaccgcat tcaccgagga
1681 cctgagcatc ccagccacat tgtgctgccg attatcaagc gaTGA G4C/S10C/L169K/G173Q-H6 (SEQ ID NO:15)
1    atggtggact gcaattacag tgttgcctgt aacgtgatgg ttccgatgcg tgatggggtg
61   cgtctggcgg tcgacctgta ccgaccagat gctgatggac ctgttccggt cctgctggtt
121  cgcaacccat acgacaagtt cgacgtgttc gcgtggtcga cgcagtcgac aaactggctt
181  gagttcgtgc gtgatggcta tgccgtggtc attcaagaca cgcgtggctt gttcgcatcg
```

Figure 13 (CONT)

```
 241 gaaggtgagt tcgtcccgca cgttgacgac gaagctgacg ccgaggatac gttgagctgg
 301 attctggaac aagcgtggtg cgacggcaat gtgggcatgt tcggcgtttc gtacttgggt
 361 gtgacccagt ggcaggccgc cgtatccggc gttggtgggc tgaaggcgat cgcgccgtcc
 421 atggcgtcgg cggacttgta ccgcgccccg tggtacggcc ctggtggtgc gctttcagtc
 481 gaggcgctgt tgggctggtc agctaagata ggtactcagc tcatcacgtc gaggtctgac
 541 gcccggcccg aagacgcagc cgacttcgtc caactcgcag caattctcaa tgacgtcgct
 601 ggcgcggcgt cggtcacgcc cctggccgag caaccgcttc tgggccgact gattccgtgg
 661 gtgatcgatc aggttgtcga tcaccccgac aacgatgaat catggcagtc cattagcttg
 721 tttgaacgac tcggcgggtt ggcaacaccg gccttgatca cggctgggtg gtacgacggg
 781 ttcgtcggcg aatcgttgcg cactttcgtt gcggtcaagg acaatgccga cgcacgtttg
 841 gttgtcggcc cttggagtca cagcaacctc actggtcgga atgcggaccg gaagttcggc
 901 attgccgcga cctacccgat tcaagaagcc accacgatgc acaaggcatt cttcgaccgg
 961 cacctccgcg gcgagaccga tgcactcgca ggcgtcccca aagtgcggct gttcgtaatg
1021 ggcatcgatg agtggcgtga cgaaacggac tggccactgc cggacacggc gtatacgccc
1081 ttctatcttg gaggtagcgg ggctgcgaat acctccacgg gtggtggaac actgtcgacg
1141 tcgatttccg gaactgaatc tgctgacacc tacctgtatg atccggccga tcccgtgcct
1201 tcgctcgggg ggacgctgct gttccacaac ggagacaacg gacccgccga ccaacgtccc
1261 attcatgacc gggacgacgt gttgtgttac agcactgagg tattgaccga cccggtggaa
1321 gtaaccggca ccgtctccgc ccggctgttc gtgtcgtcat cagcggtgga cactgatttc
1381 accgccaaac ttgtcgacgt atttcccgac ggtcgcgcga tcgcgctgtg tgacgggatc
1441 gtgcggatgc ggtaccgcga cgttggtc aatccaacct tgatcgaagc gggcgaaatc
1501 tacgaggttg ctatcgacat gcttgcaacc tcgaatgtat tcctgccagg gcatcgcatc
1561 atggtccaag tatcaagtag caacttcccg aaatacgacc gcaattcgaa taccggcgga
1621 gtaatcgcac gggaacagct cgaagagatg tgcaccgccg tgaaccgcat tcaccgagga
1681 cctgagcatc ccagccacat tgtgctgccg attatcaagc gaAAGCTTGC GGCCGCACTC
1741 GAGCACCACC ACCACCACCA CTGA
```

| Protein | Melting Temp (°C) |
|---|---|
| wtCocE | 34.77±0.02 |
| CC-CocE | 38.02±0.025 |
| CCRQ-CocE | 43.62±0.10 |
| PEG-CCRQ | 43.86±0.02 |

US 8,501,692 B2

COMPOSITIONS AND METHODS FOR ALTERING COCAINE ESTERASE ACTIVITY

CROSS REFERENCE TO RELATED APPLICATIONS

This application is a national phase application under 35 U.S.C. §371 of PCT International Application No. PCT/US2010/060278, filed Dec. 14, 2010, which claims priority to provisional application 61/286,053, filed Dec. 14, 2009, each of which are herein incorporated by reference in its entirety.

STATEMENT REGARDING FEDERALLY SPONSORED RESEARCH OR DEVELOPMENT

This invention was made with government support under DA021416 awarded by the National Institutes of Health. The government has certain rights in the invention.

FIELD OF THE INVENTION

The present invention relates to compositions and methods for treating and preventing cocaine addiction. In particular, the present invention provides mutated cocaine esterase polypeptides for use in treating and preventing cocaine addiction.

BACKGROUND OF THE INVENTION

Cocaine is considered to be the most addictive of all substances of abuse. Estimates for 2006 suggest that over half of all illicit drug-based emergency department visits involved cocaine, with 548,608 occurrences, and account for 181 visits per 100,000 people in the US.

Chronic cocaine intake causes brain cells to adapt functionally to strong imbalances of transmitter levels in order to compensate extremes. Thus, receptors disappear from the cell surface or reappear on it, resulting more or less in an "off" or "working mode" respectively, or they change their susceptibility for binding partners (ligands). However, studies suggest cocaine abusers do not show normal age-related loss of striatal DAT sites, indicating that cocaine has neuroprotective properties for dopamine neurons. The experience of insatiable hunger, aches, insomnia/oversleeping, lethargy, and persistent runny nose are often described as very unpleasant. Depression with suicidal ideation may develop in very heavy users. Finally, a loss of vesicular monoamine transporters, neurofilament proteins, and other morphological changes indicates a long term damage of dopamine neurons. All these effects contribute to a rise in tolerance thus requiring a larger dosage to achieve the same effect.

Physical side effects from chronic use of cocaine include hemoptysis, bronchospasm, pruritus, fever, diffuse alveolar infiltrates without effusions, pulmonary and systemic eosinophilia, chest pain, lung trauma, sore throat, asthma, hoarse voice, dyspnea (shortness of breath), and an aching, flu-like syndrome.

Chronic intranasal usage can degrade the cartilage separating the nostrils (the septum nasi), leading eventually to its complete disappearance. Due to the absorption of the cocaine from cocaine hydrochloride, the remaining hydrochloride forms a dilute hydrochloric acid.

Cocaine may also greatly increase the risk of developing rare autoimmune or connective tissue diseases such as lupus, Goodpasture's disease, vasculitis, glomerulonephritis, Stevens-Johnson syndrome and other diseases. It can also cause a wide array of kidney diseases and renal failure. Cocaine abuse doubles both the risks of hemorrhagic and ischemic strokes, as well as increases the risk of other infarctions, such as myocardial infarction.

The devastating medical and social cost of cocaine addiction and overdose make discovery of pharmacological agents to block the addictive effects of cocaine an important goal.

SUMMARY

The present invention relates to compositions and methods for treating and preventing cocaine addiction. In particular, the present invention provides mutated cocaine esterase polypeptides for use in treating and preventing cocaine addiction.

Embodiments of the present invention provide compositions and methods comprising mutant cocaine esterase polypeptides that have increased stability. Such polypeptides find use in neutralizing cocaine in vitro (e.g., drug screening applications) or in vivo (e.g., in drug screening and therapeutic applications).

For example, in some embodiments, the present invention provides a composition comprising a mutant cocaine esterase (CocE) polypeptide or a nucleic acid encoding such a polypeptide, wherein the cocaine esterase polypeptide has at least one mutation at the dimer interface, and wherein the mutation stabilizes the dimer interface between monomers of the CocE. In some embodiments, the mutant CocE polypeptide has an increased half life relative to wild type CocE (e.g., where the half life is at least 1 hour, at least 1 day or at least 3 days, measured in vitro or in vivo). In some embodiments, the dimer interface is stabilized by cysteine crosslinking, for example, via at least one of G4C and S10C mutations or both G4C and S10C mutations. In some embodiments, the mutant CocE polypeptide further comprises at least one additional mutation that stabilizes inter-domain or intra-domain contacts in domain II of the polypeptide (e.g., one or more of T172R, G173Q or L169K). In some embodiments, the additional mutation is T172R+G172Q or L169K+G173Q. In some embodiments, the mutant CocE polypeptide has G4C, S10C, L169K and G173Q mutations. In some embodiments, the mutant CocE polypeptide has G4C, S10C, T172R and G173Q mutations. In some embodiments, the mutant CocE polypeptide has the amino acid sequence of SEQ ID NOs: 8 or 9. In some embodiments, the mutant CocE is pegylated. In some embodiments, cysteines are introduced at positions 92 and 99 of mutant CocE polypeptides to facilitate pegylation (e.g., A92C and S99C). Such polypeptides are described, for example, by SEQ ID NOs: 18-19 and 21-22). In some embodiments, C429S and C477S mutations are introduced into CocE mutant polypeptides to decrease deleterious incorporation of PEG (e.g., described by SEQ ID NOs: 20-25).

Further embodiments of the present invention provide a method of reducing at least one biological activity of cocaine, comprising: administering a pharmaceutical composition comprising a mutant cocaine esterase (CocE) polypeptide, wherein the cocaine esterase polypeptide has at least one mutation at the dimer interface, and wherein the mutation stabilizes the dimer interface between monomers of the CocE to a subject that has or is likely to ingest cocaine. In some embodiments, the subject is addicted to cocaine or at risk of becoming addicted to cocaine. In some embodiments, the subject has ingested an overdose of cocaine. In some embodiments, the pharmaceutical composition is administered once or on an ongoing basis (e.g., as maintenance therapy). In some embodiments, the mutant CocE polypeptide has at least one of G4C and S10C mutations or both G4C and S10C mutations. In some embodiments, the mutant CocE polypeptide further comprises as least one additional mutation that stabilizes inter-domain or intra-domain contacts in domain II of the polypeptide (e.g., one or more of T172R, G173Q or L169K). In some embodiments, the additional mutation is T172R+G172Q or L169K+G173Q. In some embodiments, the mutant CocE polypeptide has G4C, S10C, L169K and G173Q mutations. In some embodiments, the mutant CocE polypeptide has G4C, S10C, T172R and G173Q mutations.

Additional embodiments are described herein.

BRIEF DESCRIPTION OF THE DRAWINGS

FIG. 12 shows amino acid sequences for wt CocE (SEQ ID NO:1), G4C/S10C CocE with H6 tag (SEQ ID NO:2), G4C/S10C/A295C CocE with H6 tag (SEQ ID NO:3), G4C/S10C/T172R/G173Q CocE with H6 tag (SEQ ID NO:4), G4C/S10C/L169K/G173Q CocE with H6 tag (SEQ ID NO:5), G4C/S10C CocE (SEQ ID NO:6), G4C/S10C/A295 CocE (SEQ ID NO:7), G4C/S10C/T172R/G173Q CocE (SEQ ID NO:8) and G4C/S10C/L169K/G173Q CocE (SEQ ID NO:9).

FIG. 13 shows nucleic acid sequences for G4C/S10C CocE (SEQ ID NO:10), CocE with H6 tag (SEQ ID NO:11), G4C/S10C/T172R/G173Q CocE (SEQ ID NO:12); G4C/S10C/T172R/G173Q CocE with H6 tag (SEQ ID NO:13), G4C/S10C/L169K/G173Q CocE (SEQ ID NO:14) and G4C/S10C/L169K/G173Q CocE with H6 tag (SEQ ID NO:15).

DEFINITIONS

Figure 1:
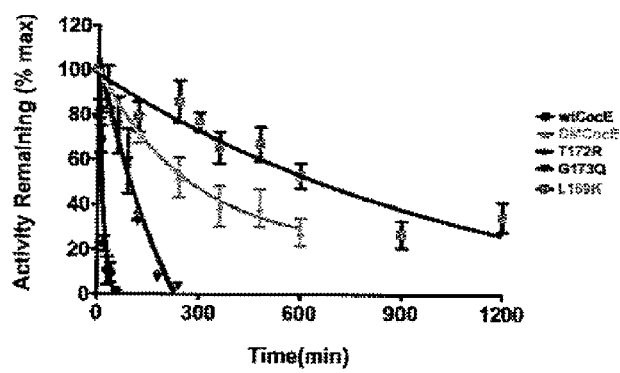
FIG. 1 shows a time course of T172R, G173Q, DMCocE and L169K activity.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "response," when used in reference to an assay, refers to the generation of a detectable signal (e.g., accumulation of reporter protein, increase in ion concentration, accumulation of a detectable chemical product).

As used herein, the term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "test compound" refers to any chemical entity, pharmaceutical, drug, and the like contemplated to be useful in the treatment and/or prevention of a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition associated with cocaine use or abuse.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

DETAILED DESCRIPTION OF THE INVENTION

The present invention relates to compositions and methods for treating and preventing cocaine addiction. In particular, the present invention provides mutated cocaine esterase polypeptides for use in treating and preventing cocaine addiction.

The mechanism by which cocaine exerts its effect is through binding monoamine transporters and blocking the re-uptake of dopamine, norepinephrine and serotonin in the synaptic junctions and potentiating the effects of neurotransmitters in the synapse. Chronic and prolonged blockade of dopamine transporters can lead to reinforcement of self-administration, and thereby to various forms of addiction (Benowitz, Pharmacol Toxicol. 72(1):3-1 (1993)). At higher concentrations, cocaine also blocks norepinephrine and serotonin reuptake transporters, which contributes to its toxic effects, including seizures, tachyarrhythmias, and sudden death (Johanson and Fischman, Pharmacol Rev. 41(1):3-52 (1989); Crumb and Clarkson, Biophys J. 57(3):589-99 (1990); Benowitz, Pharmacol Toxicol. 72(1):3-1 (1993); Uhl, Hall et al. Mol Psychiatry.; 7(1):21-6 (2002)).

Developing a classical antagonist to block the actions of a pleiotropic inhibitor like cocaine has proven difficult (Gorelick, Drug Alcohol Depend. 48(3):159-65 (1997)). Classical small molecules that compete with cocaine binding could potentially be abused as they can also have neurological effects (Gorelick, Gardner et al. Drugs. 64(14):1547-73 (2004)). To circumvent this problem, agents that intercept cocaine in the bloodstream to alter its distribution or accelerate its clearance (Gorelick Drug Alcohol Depend. 48(3):159-65 (1997); Baird, Deng et al. J Pharmacol Exp Ther. 295(3): 1127-34 (2000); Carrera, Ashley et al. Proc Natl Acad Sci USA. 98(4):1988-92 (2001); Deng, de Prada et al. J Immunol Methods. 269(1-2):299-310 (2002); Kantak, Drugs. 63(4): 341-52 (2003); Carrera, Kaufmann et al., Proc Natl Acad Sci USA. 101(28):10416-21 (2004); Meijler, Kaufmann et al., J Am Chem. Soc. 127(8):2477-84 (2005); Rogers, Mee et al., J Am Chem. Soc. 127(28):10016-7 (2005)) have been developed. In humans, cocaine is primarily metabolized to inactive products benzoic acid and ecgonine methyl ester by serum butyryl cholinesterase (BchE), which reduces the in vivo half-life ($t_{1/2}$) of cocaine to approximately 116 min. The $t_{1/2}$ can be shortened to 10 min following intravenous administration of exogenous BchE, indicating that cocaine degrading agents represent an approach to treat cocaine abuse (Lynch, Mattes et al., Toxicol Appl Pharmacol. 145(2):363-71 (1997); Browne, Slaughter et al., Biopharm Drug Dispos. 19(5):309-14 (1998). The administration of BchE or engineered mutants with enhanced catalytic activity reduces cardiovascular and psychomotor stimulant effects of cocaine in rats and mice (Carmona, Baum et al., Life Sci. 59(11):939-43 (1996); Lynch, Mattes et al., Toxicol Appl Pharmacol. 145(2):363-71 (1997); Mattes, Lynch et al. Toxicol Appl Pharmacol. 145(2): 372-80 (1997); (Gao, Atanasova et al., Mol Pharmacol. 67(1): 204-11 (2005) and can partially protect against the lethal doses of cocaine administration (Lynch, Mattes et al., Toxicol Appl Pharmacol. 145(2):363-71 (1997)).

Catalytic antibodies against cocaine (mAb antibody 15AIO) at high doses (15-50 mg/kg) (Mets, Winger et al., Proc Natl Acad Sci USA. 95(17):10176-81 (1998); Deng, de Prada et al. J Immunol Methods. 269(1-2):299-310 (2002)), and, more recently, cocaine esterase from bacteria (CocE) (Bresler, Rosser et al., Appl Environ Microbiol. 66(3):904-8 (2000)) at lower doses (1-10 mg/kg), have proven effective against cocaine-induced lethality in vivo (Cooper, Narasimhan et al., Mol Pharmacol. 70(6):1885-91 (2006); Ko, Bowen et al., J Pharmacol Exp Ther. 320(2):926-33 (2007)). The CocE gene was originally identified and isolated from *Rhodococcus* sp bacteria that grow in the rhizosphere soil surrounding coca plants and can utilize cocaine as its sole carbon and nitrogen source. The 62.5 kDa gene product is an enzyme that rapidly inactivates cocaine through hydrolysis of the cocaine benzoyl ester with a similar mechanism to buturylcholinesterase, but 800-fold faster. Injections of purified recombinant CocE have been demonstrated to protect rodents from a lethal dose of cocaine; however its duration of effectiveness is very short. CocE administration in rats or mice as little as 10 min prior to lethal doses of cocaine leads to only 67% or 50% survival, respectively (Cooper, Narasimhan et al., Mol Pharmacol. 70(6):1885-91 (2006); Ko, Bowen et al., J Pharmacol Exp Ther. 320(2):926-33 (2007)). Similarly, in vitro incubation of CocE in rat plasma or in buffer at 37° C. results in a dramatic time-dependent inactivation with $t_{1/2}$ of approximately 13 min (Cooper, Narasimhan et al. Mol Pharmacol. 70(6):1885-91 (2006)). Clearly, a more stable form of CocE is needed to exploit the superior catalytic efficiency of the enzyme for the treatment of cocaine toxicity and addiction.

Embodiments of the present invention provide stabilized CocE mutants that dramatically increase the clearance of cocaine and thus serve as useful therapeutic agents. These compositions overcome the deficiencies of the prior cocaine esterase mutants. They provide stabile, effective compositions that are suitable for use in reducing cocaine's biological effects and toxicity.

I. CocE Mutants

In some embodiments, the present invention provides CocE mutants with increased half lives. The mutants find use, for example, in increasing the clearance of cocaine. Exemplary CocE mutants are described herein.

A. Mutants

In some embodiments, mutants that increase the half life of CocE by stabilizing inter-domain or intra-domain contacts in domain II are utilized. Wild type CocE is described by SEQ ID NO:1. Exemplary CocE mutants are described, for example, by SEQ ID NOs: 2-9 and 16-25. Exemplary mutations include, but are not limited to, T172R, G173Q and L169K. In some embodiments, combinations of these mutants (e.g., T172R/G172Q or L169K/G173Q) are utilized.

In some embodiments, mutations that stabilize the dimer interface between CocE monomers are utilized to increase the stability of CocE. In some embodiments, the dimer interface is stabilized by cysteine crosslinking Examples include, but are not limited to, G4C and S10C. In some embodiments, combinations of mutations are utilized (e.g., G4C/S10C).

In some embodiments, domain II mutations are combined with dimer stabilizing mutants (e.g., G4C/S10C+L169K/G173Q or G4C/S10C+T172R/G173Q.

In some embodiments, CocE mutants exhibit increased half life (e.g., in vivo or in vitro) relative to wild type CocE. In some embodiments, half life of CocE mutants is at least 30 minutes, at least 1 hour, at least 8 hours, at least 12 hours, at least 1 day, at least 3 days, at least 1 week or at least one month.

B. Variants

In some embodiments, a variant of a CocE mutant described above can be used. Desirably, the variant of the CocE variant retains the functionality of the selected fragment. A variant of a CocE protein can be obtained by any suitable method, including random and site-directed mutagenesis of the nucleic acid encoding the CocE (see, e.g., Walder et al., Gene, 42, 133 (1986); Bauer et al., Gene, 37, 73 (1985); U.S. Pat. Nos. 4,518,584 and 4,732,462; and QuikChange Site-Directed Mutagenesis Kit (Stratagene, LaJolla, Calif.); each of which is herein incorporated by reference in its entirety).

Additionally, a variant can be synthesized using peptide-synthesizing techniques known in the art (see, e.g., Bodansky, Principles of Peptide Synthesis, Springer-Verlag, Heidelberg, 1984). In particular, a (poly)peptide can be synthesized using the procedure of solid-phase synthesis (see, e.g., Merrifield, J. Am. Chem. Soc., 85, 2149-54 (1963); Barany et al., Int. J. Peptide Protein Res., 30, 705-739 (1987), and U.S. Pat. No. 5,424,398; each of which is herein incorporated by reference in its entirety). If desired, a (poly)peptide can be synthesized with an automated peptide synthesizer. Removal of the t-butyloxycarbonyl (t-BOC) or 9-fluorenylmethyloxycarbonyl (Fmoc) amino acid blocking groups and separation of the (poly)peptide from the resin can be accomplished by, for example, acid treatment at reduced temperature. The (poly)peptide-containing mixture can then be extracted, for instance, with dimethyl ether, to remove non-peptidic organic compounds, and the synthesized (poly)peptide can be extracted from the resin powder (e.g., with about 25% w/v acetic acid). Following the synthesis of the (poly)peptide, further purification (e.g., using high performance liquid chromatography (HPLC)) optionally can be done in order to eliminate any incomplete (poly)peptides or free amino acids. Amino acid and/or HPLC analysis can be performed on the synthesized polypeptide to determine its identity. The (poly)peptide can be produced as part of a larger fusion protein, such as by the above-described methods or genetic means, or as part of a larger conjugate, such as through physical or chemical conjugation.

The variant of the above-described CocE includes molecules that have about 50% or more identity to the above-described CocE proteins. Preferably, the variant includes molecules that have 75% identity to the above-described CocE proteins. More preferably, the variant includes molecules that have 85% (e.g., about 90% or more, about 95% or more, about 96% or more, about 97% or more, about 98% or more, or about 99% or more) identity with the above-described CocE fragments. Ideally, the variant of the CocE protein contains from 1 to about 40 (e.g., about 5, about 10, about 15, about 20, about 25, about 30, about 35, or ranges thereof) amino acid substitutions, deletions, inversions, and/or insertions thereof. More preferably, the variant of the above-described CocE protein contains from 1 to about 20 amino acid substitutions, deletions, inversions, and/or insertions thereof. Most preferably, the variant contains from 1 to about 10 amino acid substitutions, deletions, inversions, and/or insertions thereof.

The substitutions, deletions, inversion, and/or insertions of the CocE protein preferably occur in non-essential regions. The identification of essential and non-essential amino acids in the CocE protein can be achieved by methods known in the art, such as by site-directed mutagenesis and AlaScan analysis (see, e.g., Moffison et al., Chem. Biol. 5(3), 302-307 (2001)). Essential amino acids should be maintained or replaced by conservative substitutions in the variants of the CocE protein. Non-essential amino acids can be deleted, or replaced by a spacer or by conservative or non-conservative substitutions.

The variants can be obtained by substitution of any of the amino acids as present in the CocE protein. As can be appreciated, there are positions in the sequence that are more tolerant to substitutions than others, and some substitutions can improve the activity of the native CocE protein. The amino acids that are essential should either be identical to the amino acids present in the CocE protein, or substituted by conservative substitutions. The amino acids that are nonessential can be identical to those in the CocE protein, can be substituted by conservative or non-conservative substitutions, and/or can be deleted.

Conservative substitution refers to the replacement of an amino acid in the CocE protein with a naturally or non-naturally occurring amino acid having similar steric properties. Where the side-chain of the amino acid to be replaced is either polar or hydrophobic, the conservative substitution should be with a naturally or non-naturally occurring amino acid that is also polar or hydrophobic (in addition to having the same steric properties as the side-chain of the replaced amino acid). When the native amino acid to be replaced is charged, the conservative substitution can be with a naturally or non-naturally occurring amino acid that is charged, or with a non-charged (polar, hydrophobic) amino acid that has the same steric properties as the side-chains of the replaced amino acid. For example, the replacement of arginine by glutamine, aspartate by asparagine, or glutamate by glutamine is considered to be a conservative substitution.

In order to further exemplify what is meant by conservative substitution, Groups A-F are listed below. The replacement of one member of the following groups by another member of the same group is considered to be a conservative substitution.

Group A includes leucine, isoleucine, valine, methionine, phenylalanine, serine, cysteine, threonine, and modified amino acids having the following side chains: ethyl, isobutyl, —CH2CH2OH, —CH2CH2CH2OH, —CH2CHOHCH3 and CH2SCH3.

Group B includes glycine, alanine, valine, serine, cysteine, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —(CH2)3COOH, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitruiine, 2-amino guanidinobutanoic acid, homologs of lysine, homologs of arginine, and ornithine.

Group F includes serine, threonine, cysteine, and modified amino acids having C1-C5 straight or branched alkyl side chains substituted with —OH or —SH.

A non-conservative substitution is a substitution in which the substituting amino acid (naturally or non-naturally occurring) has significantly different size, configuration and/or electronic properties compared with the amino acid being substituted. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, or isoleucine for glycine. Alternatively, a functional group can be added to the side chain, deleted from the side chain or exchanged with another functional group. Examples of nonconservative substitutions of this type include adding an amine, hydroxyl, or carboxylic acid to the aliphatic side chain of valine, leucine or isoleucine, or exchanging the carboxylic acid in the side chain of aspartic acid or glutamic acid with an amine or deleting the amine group in the side chain of lysine or ornithine.

For non-conservative substitutions, the side chain of the substituting amino acid can have significantly different steric and electronic properties from the functional group of the amino acid being substituted. Examples of such modifications include tryptophan for glycine, and lysine for aspartic acid.

Variants of the CocE proteins can be obtained by any suitable method, including those methods discussed above. The variants of the above-described CocE protein include molecules that have about 90% or more percent identity (e.g., about 95% or more, about 96% or more, about 97% or more, about 98% or more, or about 99% or more) with the above-described CocE proteins. Preferably, the variants of the CocE proteins contain from 1 to about 50 (e.g., about 5, about 10, about 15, about 20, about 25, about 30, about 35, about 40, about 45, or ranges thereof) amino acid substitutions, deletions, inversions, and/or insertions thereof. More preferably, the variants contain from 1 to about 30 amino acid substitutions, deletions, inversions, and/or insertions thereof. Most preferably, the variants contain from 1 to about 20 amino acid substitutions, deletions, inversions, and/or insertions thereof. Ideally, the variants contain from 1 to about 10 amino acid substitutions, deletions, inversions, and/or insertions thereof.

C. Modified Proteins

The present invention further includes proteins modified to improve one or more properties useful in pharmaceutical compounds. For example, in some embodiments, proteins are modified to enhance their ability to enter intracellular space. Such modifications include, but are not limited to, the addition of charged groups, lipids and myristate groups (See e.g., U.S. Pat. No. 5,607,691; herein incorporated by reference).

In other embodiments, the proteins of the present invention may be in the form of a liposome in which isolated protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

In some embodiments, mutant CocE proteins are pegylated. Conjugation of polymers to peptide and protein therapeutics to generate hybrid molecules with unique and distinct molecular properties has become a popular approach to alter and/or control their stability, biodistribution, pharmacokinetics and toxicology. Since the pioneering work of Abuchowski et al. (J. Biol. Chem. 252:3578-3581) of grafting polyethylene glycol (PEG) chains to albumin, PEGylation has been a very widely used conjugation approach to generate protein-polymer bio-conjugates of unique biological properties or diminished toxicities.

In some embodiments, the first step of the PEGylation of proteins and peptides involves functionalizing PEG with group specific reagents so that the conjugation of PEG to protein can be targeted to specific side chain groups of the proteins, such as amino, carboxyl, sulfhydryl or guanidino groups. In some embodiments, site directed mutagenesis is used to achieve site specific PEGylation. Cysteine (Cys) residues can be introduced in a site specific fashion in place of preselected surface amino acid residues of proteins. The thiol groups of the newly introduced Cys residues can be targeted for PEGylation using maleimide chemistry based PEG reagents. Replacement of Serine (Ser) or Threonine (Thr) with Cys has an advantage that the net charge of the mutant protein is not altered as a result of the PEGylation. In some embodiments, cysteines are introduced at positions 92 and 99 of mutant CocE polypeptides to facilitate pegylation (e.g., A92C and S99C). Such polypeptides are described, for example, by SEQ ID NOs: 18-19 and 21-22). In some embodiments, C429S and C477S mutations are introduced into CocE mutant polypeptides to decrease deleterious incorporation of PEG (e.g., described by SEQ ID NOs: 20-25).

A chemical approach to introduce new thiols on the ε-amino groups of proteins as a means of increasing accessibility of the surface amino groups for PEGylation and targeting the PEG reagents to these sites by maleimide chemistry has been developed (U.S. Pat. No. 5,585,484, herein incorporated by reference in its entirety). The initial approach involved thiolation of amino groups of proteins using 2-iminothiolane. In a preferred protocol, protein is incubated with iminothiolane in the presence of PEG maleimide, and the new thiol groups generated in situ on the protein amino groups are trapped immediately by PEG maleimide as succinimidyl derivatives. Additional methods of modifying proteins with PEG are known to those of skill in the art and are within the scope of embodiments of the present invention.

D. Nucleic Acids

In some embodiments, the present invention provides nucleic acids encoding the mutant r variant cocaine esterase polypeptides of embodiments of the present invention. Accordingly, in some embodiments, the present invention provides nucleic acids encoding cocaine esterase genes, homologs, variants (e.g., polymorphisms and mutants), including but not limited to, those described in SEQ ID NOs: 10-15. In some embodiments, the present invention provides polynucleotide sequences that are capable of hybridizing to SEQ ID NO: 10-15 under conditions of low to high stringency as long as the polynucleotide sequence capable of hybridizing encodes a protein that retains a biological activity of the cocaine esterase variants described herein. In some embodiments, the protein that retains a biological activity of the variant cocaine esterase polypeptides described herein is 70% homologous to the cocaine esterase variants described herein, preferably 80% homologous, more preferably 90% homologous, and most preferably 95% homologous to the cocaine esterase variants described herein. In preferred embodiments, hybridization conditions are based on the melting temperature (Tm) of the nucleic acid binding complex and confer a defined "stringency" as explained above (See e.g., Wahl, et al., Meth. Enzymol., 152:399-407 (1987), incorporated herein by reference).

In other embodiments of the present invention, additional alleles of cocaine esterase are provided. In preferred embodiments, alleles result from a polymorphism or mutation (e.g., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In still other embodiments of the present invention, the nucleotide sequences of the present invention may be engineered in order to alter an cocaine esterase coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of variant cocaine esterases may be extended utilizing the nucleotide sequence (e.g., SEQ ID NOs: 10-15) in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 (1993)). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 (1988)). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 (1991)). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed cocaine esterase sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

II. Drug Screening Methods

In some embodiments, the present invention provides methods of identifying additional CocE mutant proteins that have increased activity, improved stability or other desirable properties. Drug screening methods include both in vitro and in vivo assays. Exemplary screening methods are described, for example, in the experimental section below.

III. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat a variety of conditions associated with cocaine use and addiction. In addition, the compounds are also useful for preparing medicaments for treating other disorders wherein the effectiveness of the compounds are known or predicted. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In preferred embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described in above) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes.

The agents identified can be administered to subjects or individuals identified as abusing or being addicted to cocaine or individuals at risk of developing such an addiction. When the agent is administered to a subject such as a mouse, a rat or a human patient, the agent can be added to a pharmaceutically acceptable carrier and systemically or topically administered to the subject. Therapeutic amounts are empirically determined and vary with the pathology being treated, the subject being treated and the efficacy and toxicity of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing known therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations. The agent or agents to be co-administered can be for example, other agents that alter the potency or metabolism of cocaine.

IV. Therapeutic Application

In some embodiments, compositions of the present invention find use in the treatment and prevention of cocaine abuse and addiction. In some embodiments, the compositions of the present invention are administered to subjects addicted to cocaine to counteract the effect of cocaine and/or reduce the risk of overdose. In some embodiments, compositions of the present invention are administered to a subject at risk of developing an addiction to cocaine (e.g., a recreational user).

In some embodiments, the compositions of the present invention find use in research (e.g., studying physical and psychological addiction to cocaine) and screening (e.g., drug screening) applications.

Exemplary dosages and administration schedules for the therapeutic use of the compound described in are described herein. Additional administration methods and dosages are within the scope of one of skill in the art.

EXAMPLES

The following examples are provided to demonstrate and further illustrate certain preferred embodiments of the present invention and are not to be construed as limiting the scope thereof.

Example 1

Figure 2:
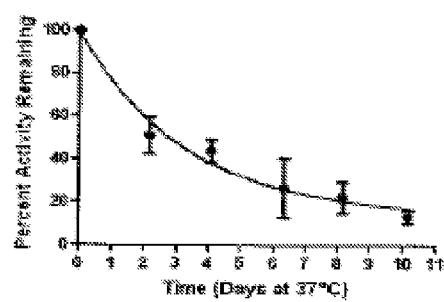
FIG. 2 shows a time course of L169K–G173Q activity.

To alleviate the thermal instability that results in the short half-life of CocE at 37° C., computational approaches were applied to predict mutants of CocE that have increased stability (Gao, Narasimhan et al. 2009). In this work a combination of molecular modeling, energy minimization, and molecular dynamics (MD) approaches using the Rosetta Design (Kuhlman and Baker 2000; Korkegian, Black et al. 2005) and AMBER programs (Case, Darden et al. 2004) were carried out. Mutating the wild type enzyme at either of two specific residues, threonine 172 or glycine 173, to arginine (T172R) and glutamine (G173Q), respectively, resulted in two different mutant forms of CocE with an in vitro half-life of 30 minutes at 37° C. Combining these two mutations to produce T172R/G172Q (RQ) CocE resulted in a synergistic effect: the half-life of RQ CocE is 4.5 hrs at 37° C. both in vitro and in vivo. A third mutation at position 169 from leucine to lysine (L169K) was also protective. The half-life of the L169K mutant form of CocE was 33 fold longer than the wild type enzyme (FIG. 1). Upon combination of this L169K mutation with the aforementioned mutations, it was found that the mutation L169K/G173Q (KQ) improved the half-life of cocaine esterase to 2.9 days at 37° C. (FIG. 2).

Figure 3:
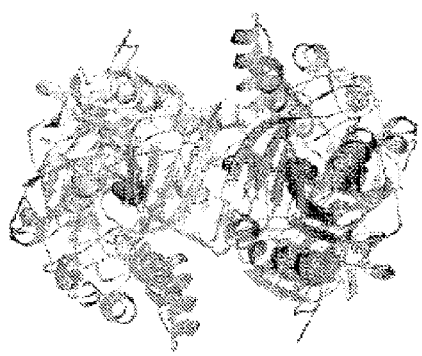
FIG. 3 shows the dimerization interface of CocE.
Figure 4:
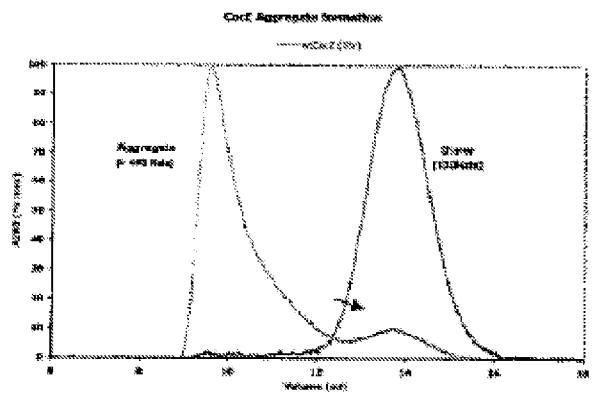
FIG. 4 shows SEC runs of wtCocE treated/untreated at 37° C.

Upon solving the crystal structures of wild-type and mutant forms of CocE, it was observed that stabilizing domain II of the enzyme, either via inter-domain (G173Q and L169K) or intra-domain (T172R) contacts enhances the thermostability of the protein. The crystal structure also revealed that CocE is likely a homodimer formed across a twofold crystallographic axis with total accessible buried surface area >1400 Å$^2$. The two monomer partners are oriented in a head to head fashion, wherein the N-terminal β-strand of each α/β hydrolase domain contributes to the β-sheet of the other α/β hydrolase domain. Residues from all three domains are involved in the formation of the dimer interface (FIG. 3). Dimers in solution are stable enough to be well resolved in a Superdex 200 size exclusion column even at low concentrations of the protein. Upon heat treatment of wild type CocE or mutant enzymes, CocE forms supra molecular aggregates which elute in the void volume of the Superdex 200 column. The time taken by each of these proteins to aggregate correlates well with their respective in vitro decay time course. Wild type starts to aggregate within 20 min of incubation at 37° C., while mutant forms take longer to aggregate.

Figure 5:
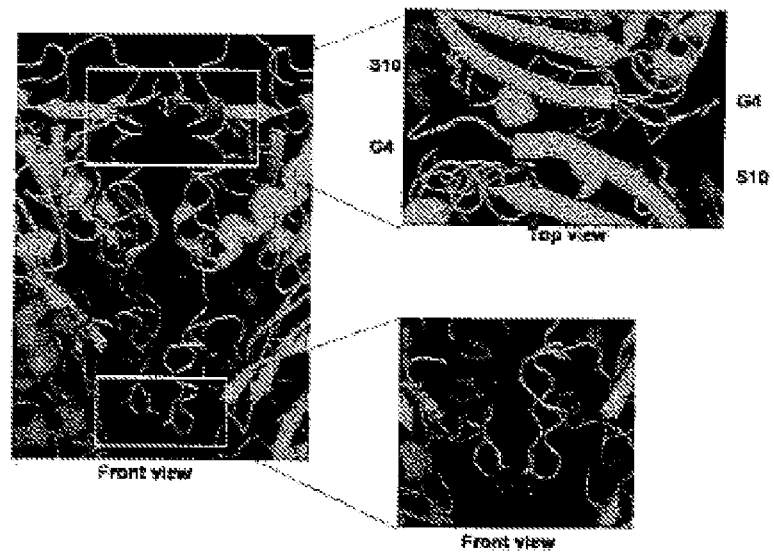
FIG. 5 shows the location of glycine at position 4, serine at position 10 and alanine at position 295 of CocE.
Figure 6:
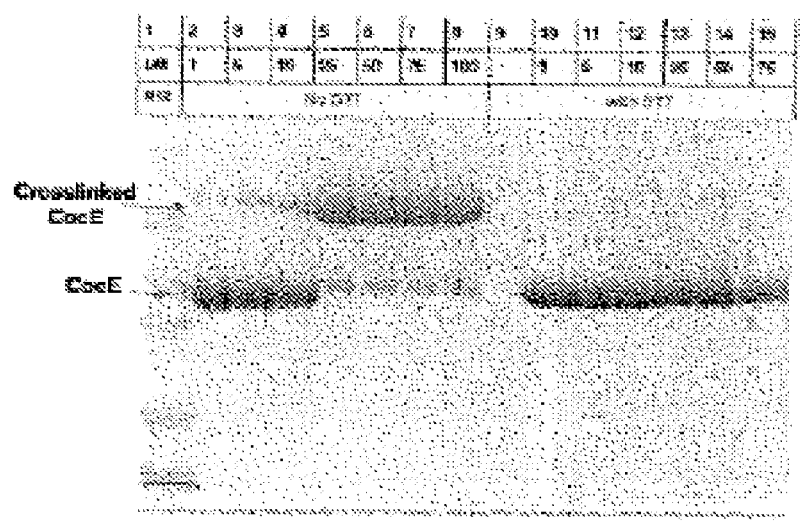
FIG. 6 shows cross-linking of CocE monomers by disulfide bridges.

Observing the kinetics of thermal stabilization of CocE and the mutants, two pathways of destabilization were observed. Local misfolding in the least stable regions within the protein leads to global misfolding and aggregation. The present invention is not limited to a particular mechanism. Indeed, an understanding of the mechanism is not necessary to practice the present invention. Nonetheless, it was contemplated that stabilizing the interface of the dimer would stabilize the protein from aggregating. This was achieved by mutating residues 4 and 10 from glycine and serine to cysteines (G4C and S10C, respectively). Glycine 4 from one partner is juxtaposed next to the side chain of serine 10 from the other subunit (FIG. 5). Alanine at 295 is also close enough that if it was mutated it will also form a disulfide bridge. It was predicted that mutating these residues to cysteines would result in formation of disulfide bridges under oxidizing conditions. G4C-S10C (CC) was cloned using site directed mutagenesis according to standard protocol and the presence of the mutations was confirmed by sequencing. The plasmid was pET22b (Novagen) grown in the presence of ampicillin and the protein was expressed with a His tag at the carboxy terminal end of the protein. The plasmid was transformed into BL21 DE3 from Novagen, protein expression was induced with 1 mM IPTG, and the mutant protein was expressed at 18° C. It was found that incubating the protein at 4° C. with 100 μM CuCl$_2$ resulted in over 95% cross-linking of the monomer as observed by SDS PAGE analysis (FIG. 6).

Figure 7:
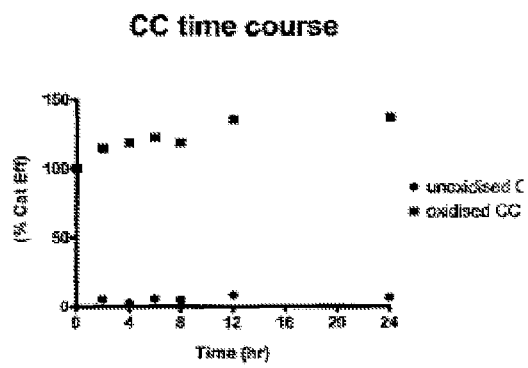
FIG. 7 shows an in vitro time course of G4C-S10C(CC mutant) activity, oxidized and unoxidized.
Figure 8:
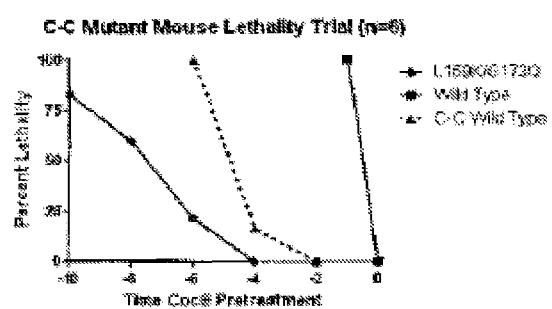
FIG. 8 shows a CC mutant in vivo protection assay.

Oxidized CC mutant did not form any observable aggregate over time. When oxidized and unoxidized forms of the CC mutant were incubated at 37° C. for different time points and aliquots from these incubations were analyzed for activity, it was found that the oxidized CC mutant was active for more than 24 hours (FIG. 7). Following heat treatment the unoxidized version of the same protein lost all its activity in less than 2 hours like wild-type CocE. The oxidized CC mutant was used in an in vivo protection assay against cocaine-induced lethality in mice. Purified protein (CC mutant) was injected (iv) into mice and at several time points prior to a lethal dose of cocaine (180 mg/kg, ip). Should the mutant enzyme be maintained in the stable form in vivo, then one would predict that the enzyme should protect the mice from the lethal effects of cocaine using longer pre-injection durations. It was determined that the CC mutant protected mice with a $t_{1/2}$ of approximately 5 hours representing a significant improvement over wild type (FIG. 8).

Figure 9:
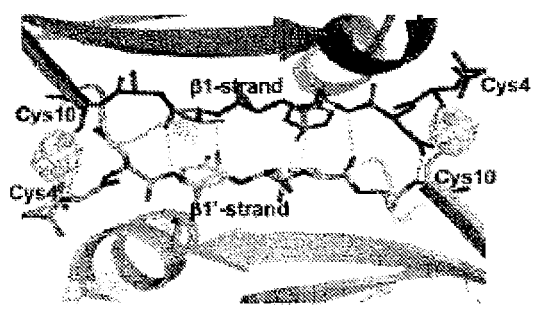
FIG. 9 shows the interface between the two monomer chains of CocE.

The crystal structure of the oxidized CC mutant revealed no gross overall changes in the structure of the protein except for the density depicting the sulfur atoms at positions 4 and 10 of each chain. The sulfur atoms were ~2 apart consistent with the distance seen in disulfide bridges in other proteins (FIG. 9).

Figure 10:
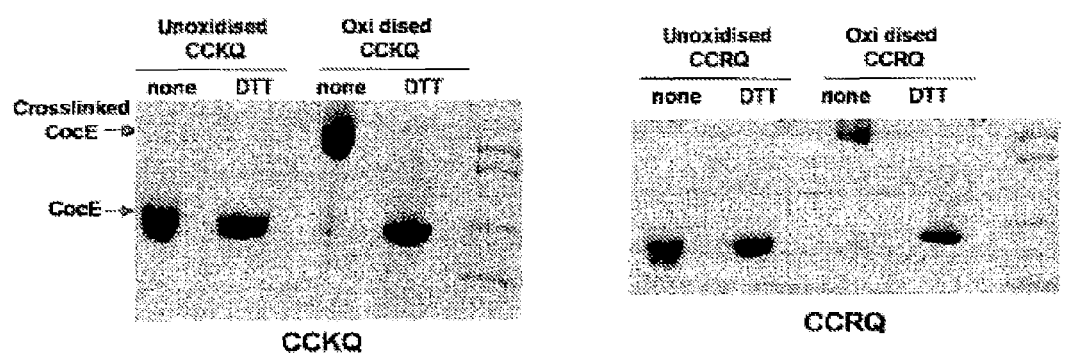
FIG. 10 shows cross-linking of CCKQ and CCRQ using 100 µM $CuCl_2$.

Mutations that stabilize the dimer form of CocE (CC) were then combined with L169K-G173Q (KQ) and T172R-G173Q (RQ) to form the CCKQ and CCRQ tetramutants. The KQ and RQ mutations stabilized the domain-domain interactions within each protein, whereas the CC mutations stabilized intrasubunit contacts. These mutants were cloned and expressed as described previously. These proteins exhibited very efficient crosslinking between subunits (FIG. 10).

Figure 11:
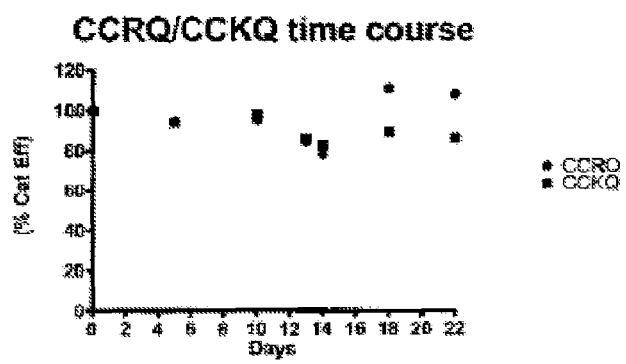
FIG. 11 shows an vitro time course depicting the stability of CCRQ and CCKQ.

Both mutants were tested with in vitro time course assays as previously described. Proteins incubated at 37° C. for more than 20 days were still nearly 100% as active as proteins freshly thawed from storage at −80° C. (FIG. 11).

CCKQ has slightly higher Vmax and Km compared to wild-type. Similar observations were made with the original LQ mutation. CCRQ has lower than expected $V_{max}$ and $K_m$, but the catalytic efficiency of both of these mutants was comparable to wild-type. In addition, both CCKQ and CCRQ appeared resistant to aggregation following treatment at 37° C. for greater than 15 days.

In summary, crosslinking the two monomer chains of CocE via disulfide bridge formation has yielded the most stable form of the enzyme measured to date. Use of this enzyme for acute and chronic cocaine abuse therapy is facilitated by the discovery of these more stable forms of the enzyme. Moreover, the problem of aggregation has been a bane for development of protein biologics for therapy, and the FDA has strict guidelines about the presence of aggregates in biological preparations. Discovery of these most stable forms of CocE eliminates the problem of aggregation during large scale production, formulation, and storage of this very important protein therapeutic drug.

Example 2

Materials and Methods

Subjects: Male NIH-swiss mice (25-30 g), and male Sprague-dawley rats (275-350 g) were obtained from Harlan (Indianapolis, Ind.), housed in a temperature-(21-23° C.), and humidity-controlled environment, on a 12-hr dark/light cycle with lights on at 6:30 AM. Mice were group housed and had free access to standard Purina rodent chow and tap water throughout the experiments with the exception of during behavioral observations. All rats were singly housed and had free access to tap water. Rats that were used for lethality studies were free-fed, whereas those used for self-administration studies were restricted to 20 g of standard Prunia rodent chow per day. One adult male rhesus monkey (*Macaca mulatta*) was singly housed in a standard stainless steel monkey cage in an environmentally controlled room (temperature 21±3° C., relative humidity 30-70%, 10-15 air changes per hour), with lights on from 07:00 to 19:00. The monkey's diet consisted of 20-50 Lab Fiber Plus Monkey Diet Chows (Lab Diet; PMI Nutrition International, LLC; Brentwood, Mo.), fresh fruit, and free access to water, and daily health checks were performed throughout the experiment.

Mouse Lethality Studies: Cocaine-induced toxicity was characterized by the occurrence of lethality, as defined by the cessation of observable movement and respiration. Prior to testing, individual mice were transferred to a clean plastic mouse cage without bedding, and allowed to habituate for 15 min after which they were placed in a small restraint chamber (outer tube diameter: 30 mm; inner tube diameter: 24 mm) to allow for the administration of CocE via tail vein injection. The tail was wiped with alcohol, and a 30½ gauge needle was used to infuse PBS, CCRQ (1.0, 10.0, or 32.0 mg/kg) or PEG-CCRQ (1.0, 10.0, or 32.0 mg/kg) into one of the side veins in a volume of 0.2 ml per mouse (n=6 per group). Sterile gauze and pressure were applied to the injection site to prevent bleeding. One minute later, 180.0 mg/kg cocaine was administered via i.p. injection, and the mouse was returned to the chamber for observation, and the presence or absence of lethality, defined as the cessation of observable movement and respiration, was recorded for 60 min thereafter. Any mice that survived were retested at 24-hr intervals using the identical procedures except the mice were not placed into the restraint tube, and no tail vein injections were administered.

Serum Collection Mice have a large vein draining the eye and submandibular area which meet at the rear of the cheek pouch. This vein provides a convenient and consistent source of blood (cheek-pouch blood sampling). A mouse bleeding lancet, (GoldenRod 4.0 mm animal lancet, MEDIpoint Inc., Mineola, N.Y.), was used to puncture this submandibular vein. Each blood sample (200 µL/mouse) was collected into a BD 400 µL microtainer tube (Fisher Scientific, Pittsburgh, Pa.) without preservatives and placed on ice for 60 min. Then, blood samples were centrifuged at 4500 rpm for 5 min at 4° C. The serum sample (50 µL/mouse) was pipetted into 2-ml cryovials (Corning Costar Co., Cambridge, Mass.) and stored at −80° C. until assayed for anti-CocE antibody titer determinations. As soon as the blood was collected, sterile gauze and pressure were applied at the puncture site to minimize the bleeding, and the mouse was returned to its home cage.

Immunological Determination A direct ELISA specific for anti-CocE antibodies was set up using a standard protocol. CocE was used (1 µg/mL) to coat a 96-well micro-titer plate using borate buffered saline (1.5 M NaCl, 0.5 M H3BO3, 1.0 M NaOH) to resuspend CocE (50 µL/well). The coating plates were left overnight at 4° C. The coating buffer was removed the following morning and the plates blocked with 2% normal goat serum in phosphate buffered saline for 1 h at 37° C. and washed 3 times. Serum from the various groups of mice was serially diluted in 50 µL of phosphate buffered saline in the wells in a range of $10^2$ to $10^7$ and run in duplicate. The plates were covered and incubated for 1 h at 37° C. Subsequently, the plates were washed 3 times and 50 µL/well of goat anti-mouse IgG peroxidase labeled antibody diluted 1:400. The plates were then washed 3 times and 100 µL peroxidase substrate solution (OPD dissolved in citrate/phosphate buffer) was added to each well. After a 5-10 min incubation (based upon color development in the positive controls), the reaction was stopped using 3M $H_2SO_4$ (50 µL/well). The plates were read at 490 nm and titer was determined by the highest dilution that showed increases over background absorbance.

Data analysis Data from the behavioral toxicity studies (% of mice showing affected responses) were analyzed with Fischer's exact probability test with one tail. Mean values (mean±S.E.M.) were calculated from individual values for increased titer numbers. These data were analyzed by one-way analysis of variance (ANOVA) followed by the Newman-Keuls test for multiple (post hoc) comparisons. The criterion for significance was set at $p<0.05$.

Rat Studies:

Surgical Preparation Prior to experimentation, all rats were surgically prepared with a chronic indwelling catheter in either their left jugular (lethality) or left femoral (self-administration) vein which exited between the scapula under ketamine:xylazine (90:10 mg/kg; i.p.) anesthesia. For self-administration studies this catheter was attached to a metal button tether, which was sutured to the muscle between the scapula. All rats were allowed 5-7 days to recover, and catheters were flushed with 0.2 ml of heparinized saline (100 U/ml) during recovery, as well as before and after each session to insure patency.

Lethality Studies Rats (n=6 per group) were individually placed in a test chamber (49 cm L×23 cm W×21 cm H clear shoe box rodent cage with standard cob bedding) 30 minutes prior to pretreatment with PBS, CCRQ (32.0 mg/kg), or one of three doses of PEG-CCRQ (3.2, 10.0, or 32.0 mg/kg) administered 1-min prior to an LD100 dose of cocaine (180.0 mg/kg; i.p.). Following cocaine administration, the presence or absence of lethality, defined as the cessation of observable movement and respiration, was recorded for 60 min. Any rats that survived were retested at 24-hr intervals using the identical procedures except no i.v. infusions were administered prior to dosing with 180.0 mg/kg cocaine.

Self-Administration Studies All experimental sessions were conducted in operant conditioning chambers (30.5 cm W×24 cm D×21 cm H; Med Associates Inc., St. Albans, Vt.) placed inside sound attenuating cubicles. Each chamber was equipped with a nosepoke device and a lever located on one wall (ENV-110M, ENV-114BM; Med Associates Inc.), and a white houselight located on the opposite wall. The nosepoke could be illuminated with a yellow stimulus light, and a set of green, yellow, and red LED stimulus lights was located above both the nosepoke and lever. A syringe pump (PHM-100; Med Associates Inc.) allowed for drug delivery through Tygon® tubing connected to a fluid swivel (Instech Laboratories Inc, Plymouth Meeting, Pa.) and spring tether which was held in place by a counterbalanced arm.

All rats (n=6) were initially trained to nosepoke for 0.32 mg/kg/inj cocaine during daily, 60-min sessions under a fixed ratio (FR) 1 schedule of reinforcement. Illumination of the yellow nosepoke light signaled cocaine availability, and subsequent nosepokes resulted in an injection accompanied by the illumination of the three LEDs above the nosepoke, followed by a 5 sec timeout (TO) during which time the houselight was illuminated and responses were recorded but had no scheduled consequence. During operant training the schedule requirements were progressively increased (FR1, FR2, FR3, and FR5) until responding for 0.32 mg/kg/inj cocaine was maintained under a FR5TO5. Upon stabilization of responding, rats were switched to a five-component FR5TO5 schedule during which rats could earn either 0.0, 0.032, 0.1, 0.32, or 1.0 mg/kg/inj cocaine in successive 25-min components. Components were separated by a 2-min blackout during which time the houselight was on, and each component began with a non-contingent injection of the dose of cocaine that was available for injection.

Once responding stabilized in each of the five components, a single session saline substitution was performed to allow for the effects of PEG-CCRQ on cocaine-maintained responding to be compared to those observed with the acute removal of cocaine. PEG-CCRQ (3.2, 10.0, and 32.0 mg/kg; i.v.) was administered immediately before the start of sessions in which cocaine was available for injection, with the order of the doses randomized and separated by at least 7 days.

Rhesus Monkey Studies:

Surgical preparation A rhesus monkey was implanted with a radio-telemetric probe (D70-PCT; DSI Inc., St. Paul, Minn.) to allow for the real-time collection of cardiovascular measures, as well as an indwelling venous catheter to allow for drug delivery. Prior to surgery, the monkey was anesthetized with ketamine (10.0 mg/kg; i.m.) and placed on a heating pad set to maintain the animal's body temperature at approximately 37° C. The monkey was prepared by shaving the hair along the right flank, above the right femoral artery, just above the zyphoid process and to the right of the right clavicle. All areas were scrubbed with alternating betadine/alcohol swabs and small incisions were made to allow for the implantation of the probe. The blood pressure catheter implanted in the femoral artery, and ECG leads were sutured to the muscle above the zyphoid process, and clavicle. All incisions were closed with 5-0 Ethilon® suture, and the monkey was allowed 5-7 days to recover from surgery prior to implantation of an indwelling catheter in right femoral vein. The areas between the scapula, and above the right femoral vein were shaved and scrubbed with alternating betadine/alcohol swabs, and small incisions were made to allow for catheter implantation. Upon implantation, the catheter exited the monkey from the incision between the scapula, and the monkey was then fitted with a mesh jacket, and attached to a steal tether on a swivel to allow for unrestrained movement in the home cage. A 7-day recover period was again provided prior to experimentation during which time the catheter was flushed daily with 3 ml of saline to ensure catheter patency.

Effects of PEG-CCRQ on cocaine-induced increases in mean arterial pressure and heart rate The capacity of PEG-CCRQ to alter the cardiovascular effects of cocaine was evaluated in one rhesus monkey. Two infusions, spaced 10-min apart, were administered during each session. In order to first determine the effects of cocaine alone, 3.2 mg/kg; i.v. cocaine was followed 10-min later by PBS, and compared to the effects of saline followed 10-min later by PBS. One week after the initial dose of 3.2 mg/kg cocaine, a second 3.2 mg/kg; i.v. dose of cocaine was administered, however, 3.2 mg/kg; i.v. PEG-CCRQ was administered instead of PBS. Following dosing with PEG-CCRQ, the cocaine-PBS condition was repeated daily until the cardiovascular effects of cocaine returned to baseline. Each infusion was followed by a 5 ml saline flush to ensure the entire dose was delivered, and real-time measures of MAP, HR, core body temperature, and locomotor activity were collected at 1-sec intervals for at least 30 minutes before, and 50 minutes after cocaine administration.

Materials: Cocaine was purchased from Mallinckroft Inc. All other reagents are of analytical grade and were obtained from Fisher Scientific or Sigma-Aldridge Corp. Branched 40K PEG was purchased from Gen Chem. Inc.

Site Directed Mutagenesis: pET22b (+) CocE plasmid was provided by The Scripps Institute, CA (Turner et al., (2002) *Biochemistry* 41, 12297-12307). Wild-type (wt-CocE) and CocE mutants were expressed as C-terminal hexahistidine-tagged proteins containing the exogenous sequence KLAAALEHHHHHH (SEQ ID NO:1) at the C-terminus. Point mutations were generated using a modified QuikChange™ (Stratagene) mutagenesis protocol. To generate double mutants, cDNAs with single point mutations were used as templates for a second round of mutagenesis. Oligonucleotide primer sequences are available on request. All mutants were confirmed by sequencing of both strands over the entire coding region. CocE preparations were expressed in *E. coli* BL-21 Gold (DE3) cells grown at 37° C. to an $OD_{600}$ of 0.8. Protein expression was induced with 1 mM isopropyl-β-thiogalactopyranoside and cells were harvested after incubation for 12 hours at 18° C.

Purification of cocaine esterase and mutants Cells were pelleted, resuspended in 50 mM Tris-HCl, pH 8.0, 150 mM NaCl supplemented with protease inhibitors (3 μg/ml each of leupeptin and lima bean or soybean trypsin inhibitor), and lysed using a French press. Wild type or mutant CocE was enriched using Talon™ metal chelate affinity chromatography (Clontech Laboratories, Inc.), followed by anion-exchange chromatography on a Q-Sepharose fast performance liquid chromatography (FPLC) column (GE Healthcare). CocE was eluted from the Q-Sepharose column with a 150-450 mM NaCl linear gradient in buffers containing 50 mM Tris pH 8.0. The peak fractions were pooled and concentrated typically to 5 mg/ml using Centricon-30 concentrators (Millipore), and then snap frozen in liquid nitrogen and stored at −80° C.

Oxidation: Purified proteins were oxidized in 50 mM Tris pH 8.0 buffer containing 100 μm $CuCl_2$ overnight at 4° C. $CuCl_2$ was then removed by chelating it by adding 1 mM EDTA to the above mixture. Protein was further purified by passing it through Q Sepharose column and eluting off the column with 150-500 mM NaCl gradient. Fractions containing purified oxidized protein were identified by running on a SDS-PAGE gel under non-reducing conditions and pooled and concentrated to 5 mg/ml and snap frozen in liq $N_2$ and stored at −80° C.

PEGylation: Oxidized proteins were conjugated with maleimide linker containing branched PEG 40K (Genchem) over night in phosphate buffered saline (pH 8.0). The mixture was then loaded on to a Q sepharose column (GE Healthsciences) and eluted off the column over a 100 mM-500 mM NaCl gradient in a 50 mM Tris, pH 8.0 buffer. PEGylated CCRQ proteins eluted off the column earlier than unPEGylated CCRQ. Fractions collected were analyzed in a SDS PAGE gel and PEGylated CCRQ were pooled and concentrated.

Michaelis-Menten kinetics of cocaine hydrolysis: A spectrophotometric real-time assay was used to monitor cocaine hydrolysis (Xie et al., (1999) *Mol Pharmacol* 55, 83-91). The initial rates of decay were determined by following the change in the intrinsic absorbance of cocaine at 240 nm (6700 $M^{-1}$ $cm^{-1}$) (Xie et al., supra) on a SpectraMax Plus 384 UV plate reader (Molecular Devices) using SOFTmax Pro software (Version 3.1.2). The reaction was initiated by the addition of 100 mL of wt-CocE or mutant CocE (50 ng/mL, 25 ng/mL, 10 ng/mL or 5 ng/mL) made in phosphate buffered saline (PBS) pH 7.4 to 100 µL of a 2× cocaine solution made in PBS. The final enzyme concentration was 25 ng/mL, 12.5 ng/mL, 5 ng/mL or 2.5 ng/mL and the final cocaine concentrations were: 100, 50, 25, 12.5, 5, 2.5, 0.5, and 0.25 µM. $V_{max}$ and $K_m$ values were calculated using Prism (GraphPad Software). For stability measurements, wt-CocE or mutant CocE was diluted to 50 ng/mL (2×) concentration and incubated at 37° C. Aliquots were removed at varying time points and assayed for activity against cocaine as described above (n of 5). Temperature-dependent decay in esterase activity was measured by pre-incubating wt-CocE and mutant forms of CocE (50 ng/mL) at various temperatures (0, 25, 35, 37, 42, 45, 48, 50 and 55° C.) for 30 min and the activity remaining was measured as described above. These experiments were done in duplicates at two separate times (n=2).

Melting Temperatures ($T_m$) Measurements Using Thermo Fluor: Purified wt-CocE and mutants CC, CCRQ and CCKQ were buffer exchanged into 50 mM Tris, pH8.0. Five µL of 0.2 mg/mL protein were placed in an ABgene 384-well PCR (Thermo-Fisher) plate in triplicate. Five µL of 200 µM dye 1-anilinonaphthalene-8-sulfonic acid (1,8-ANS) (Sigma) was subsequently placed on top of the protein solution. The plates were spun on Beckman-Coulter centrifuge at 1000×g for 2 min to remove air bubbles. One µL of mineral oil was overlaid on top of the protein-dye mix to prevent evaporation. Protein unfolding was monitored on a Thermo Fluor 384 reader (Johnson and Johnson) using a temperature gradient ranging from 25 to 85° C. The fluorescence emission data were analyzed using Thermo Fluor Acquire 3.0 software as per manufacturer's guidelines.

Crystallization and Data Collection: Crystals were grown by hanging-drop vapor diffusion in VDX plates. One micro liter of CocE at 8 mg/ml was added to one micro liter of mother liquor on a siliconized glass cover slip and incubated above one mL of mother liquor. Crystals containing one monomer per asymmetric unit were grown and harvested as described previously (Narasimhan et al., (2010) *Protein Eng Des Sel*). A second crystal form was obtained with mother liquor consisting of 20% Polyethylene Glycol (PEG) 3,350, 100 mM 2-(N-Morpholino) Ethane Sulfonic Acid (MES) pH 6.0, and 1 M NaCl. Drops were incubated on siliconized cover slips at 4° over 1 mL of mother liquor. The PEG crystal-form was harvested in cryoprotectant containing 70% mother liquor and 30% glycerol. All data was collected at LS-CAT of the Advanced Photon Source, indexed and scaled using HKL2000 (Otwinowski and Minor, (1997) In *Methods in Enzymology* (Charles W. Carter, Jr., Ed.), pp 307-326) built using Coot (Emsley and Cowtan, (2004) *Acta Crystallogr D Biol Crystallogr* 60, 2126-2132) and refined using Refmac 5.2.2 (Vagin et al., (2004) *Acta Crystallogr D Biol Crystallogr* 60, 2184-2195).

Results

Figure 14:
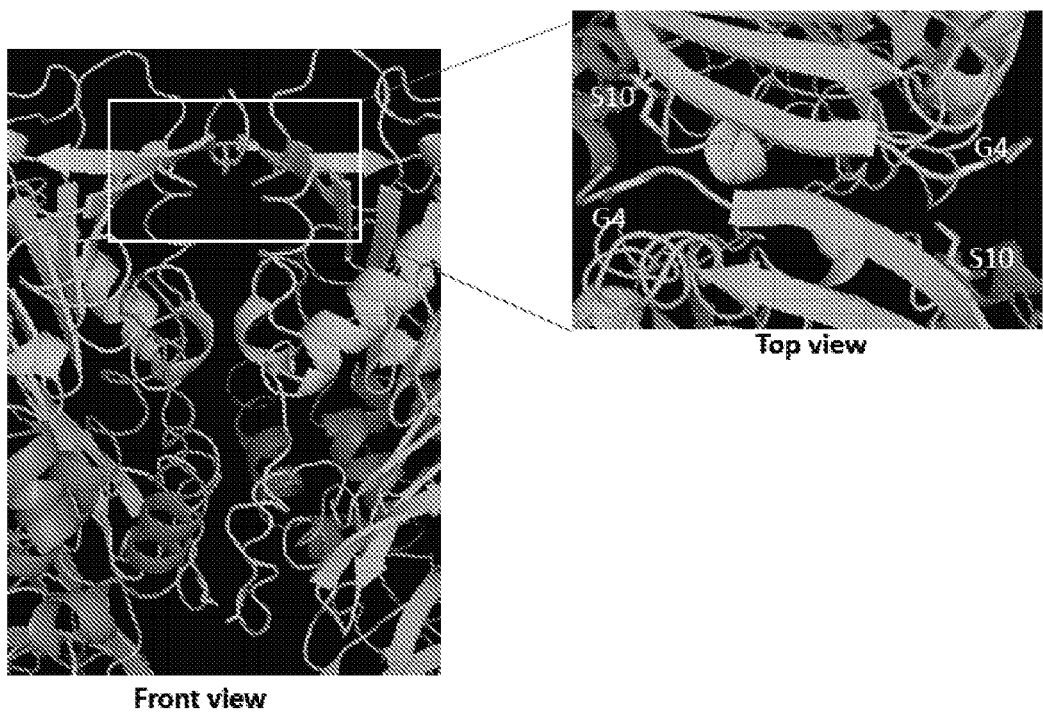
FIG. 14 shows wt-CocE dimer interface and position of β1-strands that forms a continuous β-sheet. A) Front view of wt-CocE dimer interface. B) Top view of wt-CocE dimer interface showing β1-strands of both monomer partners depicting glycine at position 4 and serine at position 10 in each of the monomer chains.

Placement of new cysteines: It was previously reported that wt-CocE is a homodimer (Narasimhan et al., (2010) *Protein Eng Des Sel*). Analysis of the structure revealed many potential sites where cysteines could be placed, which under oxidizing conditions would form disulfide bridges that would crosslink the dimer interface. It was predicted that glycine at position 4 in one monomer chain (G4) and serine at position 10 (S10) in its partner when substituted to cysteines would create the right bond angle and distance (Sowdhamini et al, (1989) *Protein Eng* 3, 95-103) to form a disulfide bridge (FIG. 14). G4C-S10C(CC-CocE) double mutations were incorporated into wt-CocE and previously described thermostabilizing mutant, RQ (Narasimhan et al. (2010) *Protein Eng Des Sel*.) to create CC-CocE and CCRQ-CocE tetra mutant form of CocE and the proteins were expressed in BL21 (DE3) cells and purified as described previously (Narasimhan et al, supra). Purified proteins were oxidized in the presence of 100 mM $CuCl_2$ overnight at 4° C. and the oxidized proteins were purified on an Q-Sepharose column.

Figure 15:
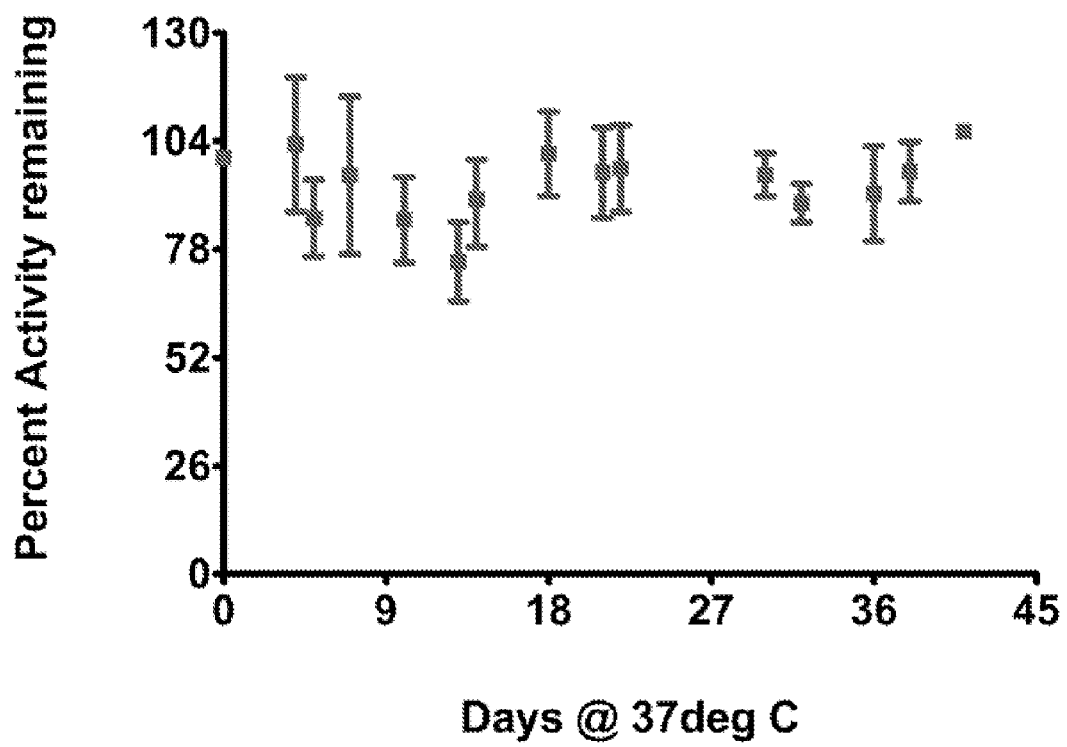
FIG. 15 shows enzymatic stability of CCRQ-CocE. A) Decay in the capacity to convert cocaine to ecgonine methylester and benzoic acid was measured at 37° C. B) Melting temperatures of wild-type and mutants forms of CocE. C) Temperature-dependent decay in esterase activity.

Stability assessment: Purified proteins were assessed for cocaine hydrolyzing activity as described previously and found them to be as active as wt-CocE (Table I) (Narasimhan et al, supra). CC-CocE protein retained 100% enzymatic activity even after 7 days of incubation at 37° C. In CCRQ-CocE, the tetra mutant form of CocE, these substitutions acted synergistically to create a meta-stable form of CocE, which retained 80% of enzymatic activity after a 40-day incubation at 37° C. (FIG. 15A). Thermofluor analysis was performed on CC-CocE and CCRQ-CocE to monitor protein unfolding and predict melting temperatures ($T_m$). CC protein had slightly elevated $T_m$ as compared to wt-CocE (34.77° C. Vs 38.02° C.) and CCRQ had a $T_m$ of 43.86° C., which is 9 degrees higher than wt-CocE, consistent with increased life of these forms of CocE at 37° C. (FIG. 15B and Table 1). Thermal inactivation assays were performed as described (Narasimhan et al, supra), in proteins were pre-incubated at temperatures above 37° C. prior to measuring their activity. It was shown that wt-CocE gets inactivated within 30 mins at 30° C., whereas RQ CocE and L169K variants get inactivated at higher temperature (40-45° C.) (Narasimhan et al, supra). CCRQ retained 90% of activity even after 15 min incubation at 47.5° C., indicating the improved thermostability over RQCocE (FIG. 15C). Size-exclusion chromatography analysis revealed that even after 7-day incubation at 37° C., the majority of CCRQ-CocE protein resolved at approximately 140 Kda (dimer CocE size) with very little showing up in the void volume corresponding to aggregated protein, as opposed to wt-CocE which aggregated within an 1 hour incubation at 37° C. (Narasimhan et al, supra).

Figure 16:
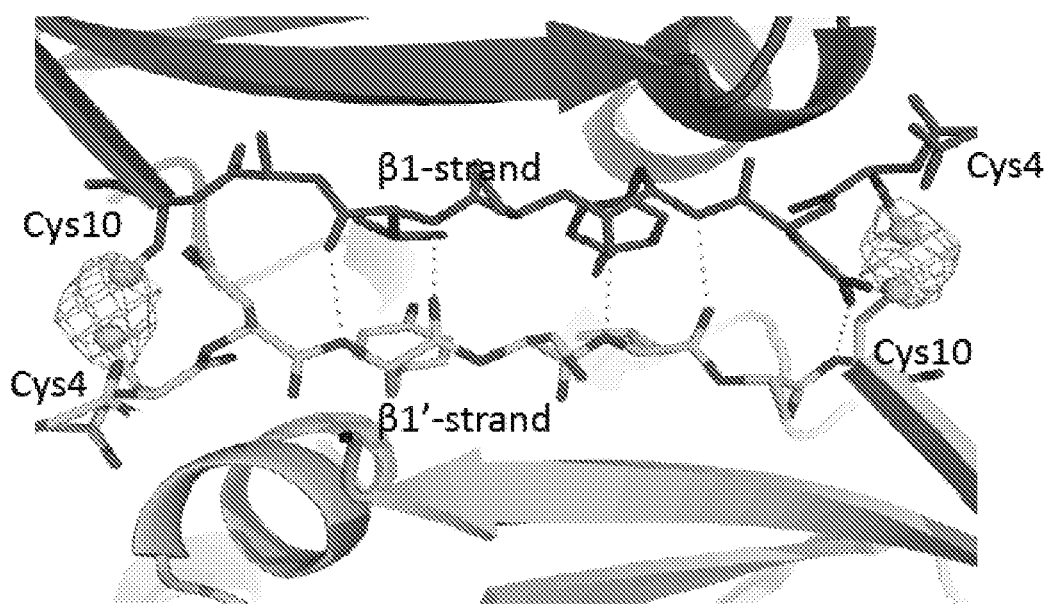
FIG. 16 shows x-ray crystallographic analysis of CC-CocE to show proximity of sulfur atoms in cysteine 4 and 10.

Structure analysis: X-ray crystal structures of CC and CCRQ were determined as described previously and a second crystal form obtained with PEG 3350 as a cryoprotectant was also solved. Both the crystal forms showed similar structures and there was good density showing the sulfur atoms in close proximity (2.08 Å) at residues 4 and 10 confirming the presence of these mutations. The distance and angle between the sulfur atoms were ideal for the formation of a disulfide bridge across the dimer interface (FIG. 16). The RMSD deviation between the wt-CocE and CC-CocE, and between RQ-CocE and CCRQ was negligible.

Figure 17:
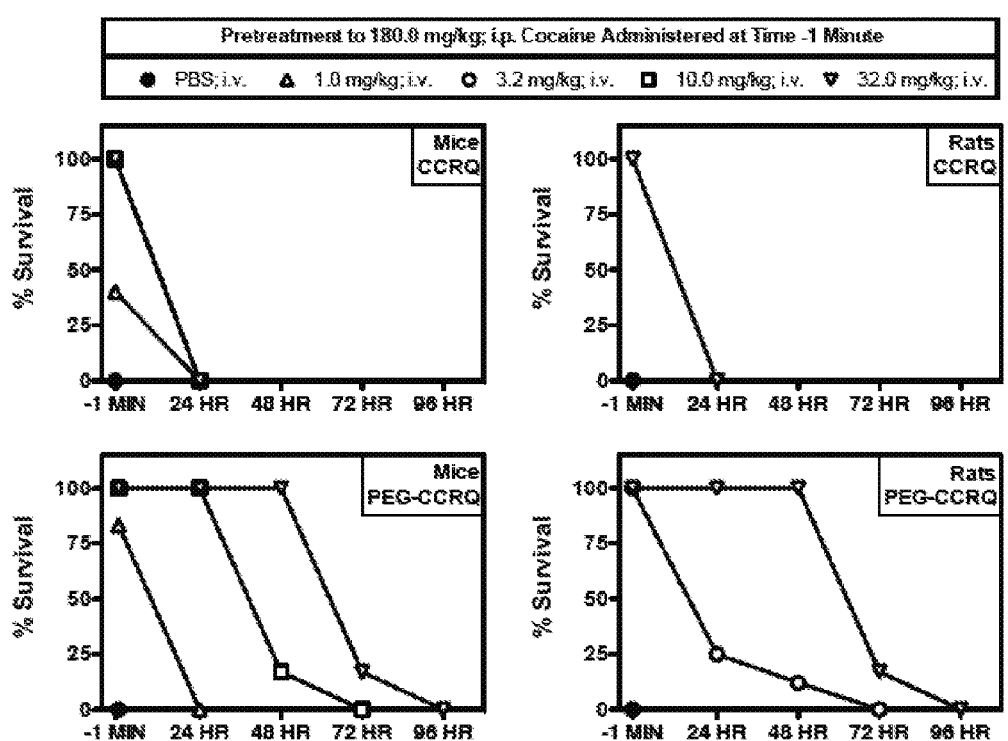
FIG. 17 shows efficacy of CCRQ-CocE or PEG-CCRQ CocE in vivo. 1 mg/kg (triangles), 10 mg/kg (squares) or 32 mg/kg (inverted triangles) of CCRQ (top panels) or 1 mg/kg (triangles), 3.2 mg/kg (open circles), 10 mg/kg (squares) or 32 mg/kg (inverted triangles) of PEG-CCRQ (bottom panels).

In vivo protection: The ability of CCRQ-CocE to protect rodents from injections of lethal doses of cocaine was determined as described in Narasimhan et al (supra). wt-CocE pretreated mice succumbed to lethal dose of cocaine as shown before (Narasimhan et al, supra). Animals pretreated for longer than 6 hours with CC-CocE didn't survive, but more than 80% survived the 4-hr pretreatment condition. To ascertain if the more thermally stable CCRQ (FIG. 17) performed better in vivo, mice were pretreated with CCRQ at 0.1 mg/kg, 1 mg/kg (triangles), 10 mg (squares) or 30 mg (closed circles) at various times prior to lethal cocaine injection (i.p.). Pretreatment of animals with CCRQ was not effective for longer than 24 hours even at the highest dose tested. Similar results were obtained with 30 mg CCRQ-CocE (closed circles) in rats (FIG. 17, Right top panel).

Figure 23:
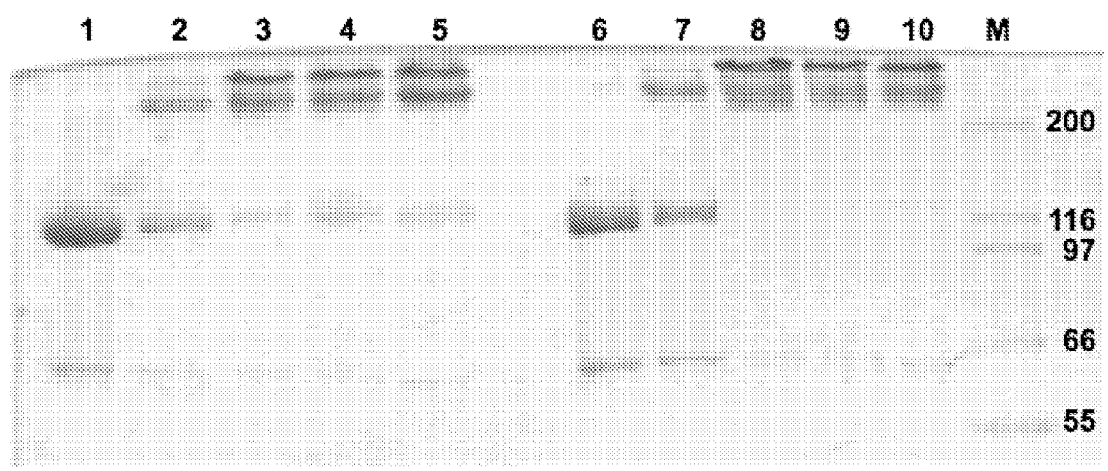
FIG. 23 shows an SDS-PAGE gel depicting the mobility and the approximate size of PEGylated CC-CoCE (lanes 2, 3, 4, and 5) and PEGylated CCRQ-CocE (lanes 7, 8, 9 and 10).

CCRQ-CocE protein was PEGylated with 40-Kda branched PEG using maleimide cross-linking to prolong the in vivo life-time of the protein (Park et al., (2010) *J Control Release* 142, 174-179). CC-CocE or CCRQ-CocE were conjugated to 40-Kda branched PEG with a molar ratio of 1:1, 1:5, 1:10 or 1:20 to test the best possible condition for conjugation. No difference in the appearance or yield of PEGylated CocE protein was observed when protein to PEG ratio was greater than 1:5 (FIG. 23). PEG CCRQ-CocE was separated from native-CocE by ion-exchange chromatography and purified to 100% homogeneity. PEG-CCRQ migrated slower compared to CCRQ-CocE on a 4-20% gradient SDS-PAGE gel (FIG. 23) consistent with their higher molecular weight and hydrodynamic radius. PEG-CCRQ is as active as wt-CocE in hydrolyzing cocaine (Table 1). PEG-CCRQ predictably had higher melting temperature ($T_m$) as compared to wt-CocE (43.86° C. Vs 34.77° C.) when observed by Thermofluor experiments (FIG. 15B and Table 1).

PEG-CCRQ Rodent Lethality studies: To observe protection of rodents against from lethal doses of cocaine, we pretreated mice (FIG. 17, bottom left panel) and rats (FIG. 17, bottom right panel) with PEG-CCRQ (1, 10 or 32 mg/kg per mice and 3.2, 10.0 or 32 mg/kg per rat) intravenously 1-min prior to the initial dose of cocaine (180.0 mg/kg; i.p.), with subsequent doses of cocaine (180 mg/kg) administered at 24-hr intervals. At this dose of cocaine, rodents die within 3-5 minutes of injection if no CocE was given either prior or subsequent to cocaine injection. Although unPEGylated CCRQ provided a dose-dependent protection against the lethal effect of cocaine (FIG. 17), pretreatment with PEG-CCRQ provided a dose- and time-dependent protection against an LD100 dose of cocaine in both rats and mice (FIG. 17, bottom panels). Unlike the protective effects of CCRQ (3.2-32.0 mg/kg), which had fully dissipated 24-hrs after administration, the protective effects of pretreatment with PEG-CCRQ were much longer lasting. When administered at a dose of 10 mg/kg dose (open squares) PEG-CCRQ provided a complete protection against a second challenge dose of 180.0 mg/kg; i.p. cocaine when administered 24-hr later, with all mice and rats dying by the fourth challenge dose administered 72 hours later. Similar effects were observed with a dose of 32 mg of PEG-CCRQ (open, inverted triangles), with all mice and surviving the third challenge dose administered 48 hours after pretreatment with PEG-CCRQ, and 100% lethality observed at the fifth challenge dose 96-hrs later.

Figure 18:
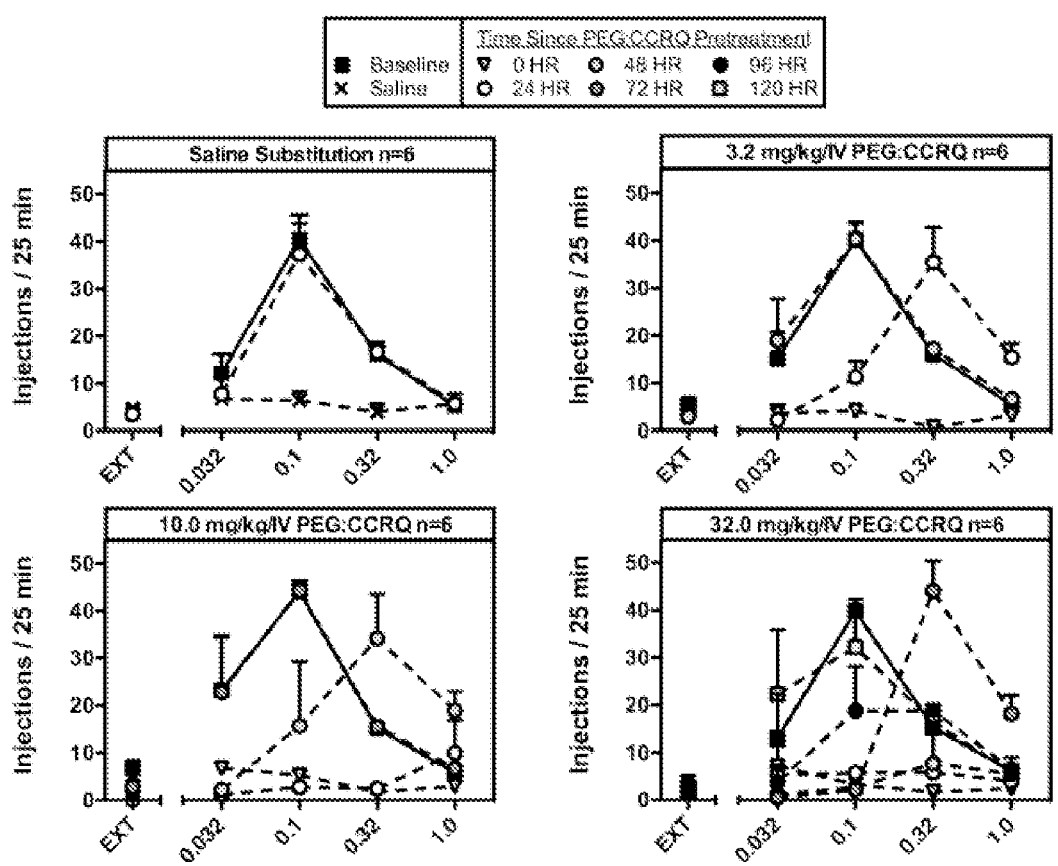
FIG. 18 shows PEG-CCRQ mediated suppression of cocaine self-administration in rats. Rats were trained to respond for increasing doses of cocaine under a fixed ratio (FR) schedule of reinforcement during five sequential components.

PEG-CCRQ Self-administration: Rats were trained to respond for increasing doses of cocaine under a fixed ratio (FR) schedule of reinforcement during five sequential components. To evaluate whether PEG-CCRQ can attenuate responses for longer periods of time (FIG. 18), rats were pretreated with saline, 3.2 mg/kg, 10 mg/kg or 32 mg/kg PEG-CCRQ at immediately before the start of a session (Time 0; inverted triangles), and re-tested at 24-hr increments until responding for cocaine returned to baseline-like levels. During baseline sessions in which rats were pretreated with saline, the dose-response curve for cocaine-maintained responding was inverted U-shaped, with very low rates of responding maintained by either no (EXT), or a low unit-dose of cocaine, peak responding maintained by 0.1 mg/kg/inj cocaine, and dose-dependent decreases in responding maintained by doses of 0.32, and 1.0 mg/kg/inj cocaine. Conversely, when saline was substituted for cocaine, low rates of responding were observed in each of the five components, with returning to baseline levels with the reintroduction of cocaine 24-hr later (FIG. 18; top left panel). Similar to when saline was substituted for cocaine, low rates of responding were observed when rats were pretreated with 3.2 mg/kg PEG-CCRQ and allowed to respond for cocaine (0, 0.032, 0.1, 0.32, and 1.0 mg/kg/inj), with a partial recovery of cocaine-maintained responding observed 24-hr later, and baseline-like levels of responding observed 48-hr after pretreatment with PEG-CCRQ. A similar suppression of responding was observed immediately after pretreatment with 10 mg/kg PEG-CCRQ, however, unlike with 3.2 mg/kg PEG-CCRQ, these low rates of cocaine-maintained responding were also observed 24-hr later, with a partial recovery of responding observed 48-hr later, and baseline-like rates of responding observed 72-hr after PEG-CCRQ administration. At the highest dose tested (32 mg/kg PEG-CCRQ), cocaine-maintained responding occurred at saline-like rates for the first 48-hr after administration, with a partial recovery of responding observed at the 72-hr time point, however, baseline-like rates of responding were not fully recovered until five days, or 120-hr after the administration of PEG-CCRQ.

Figure 19:
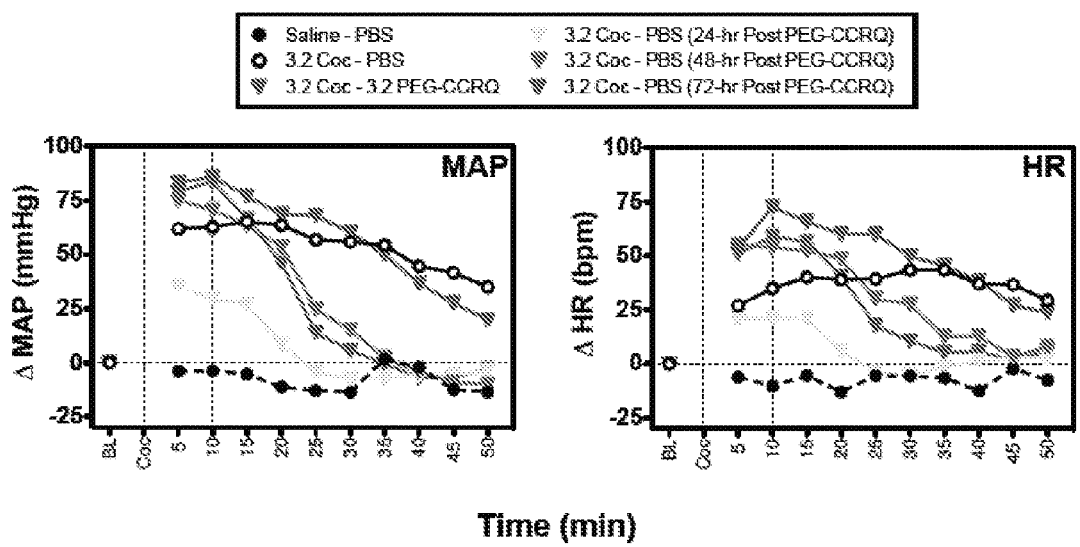
FIG. 19 shows the effect of PEG-CCRQ on the cardiovascular effects of cocaine in monkeys. Monkeys were either given saline (closed circles) or 3.2 mg/kg cocaine (open circles) intravenously and mean arterial pressure (MAP, left panel) and heart rate (HR, right panel) were observed.

PEG-CCRQ decreases cardiovascular effects of cocaine in rhesus monkey: When compared to saline (filled circles), 3.2 mg/kg; i.v. cocaine (open circles) produces a long-lasting increase in mean arterial pressure (MAP) and heart rate (HR). As shown in FIG. 19, these increases in MAP and HR were rapidly decreased following the administration of 3.2 mg/kg PEG-CCRQ, 10-min after cocaine. In addition to this immediate amelioration of the cardiovascular effects of cocaine, the protective effects of PEG-CCRQ against the increases in MAP and HR induced by additional challenge doses of 3.2 mg/kg cocaine were still apparent at the 24-hr and 48-hr time points, however, these effects had diminished by the 72-hr time point, and the cardiovascular effects of cocaine were no different than during the baseline condition.

Figure 20:
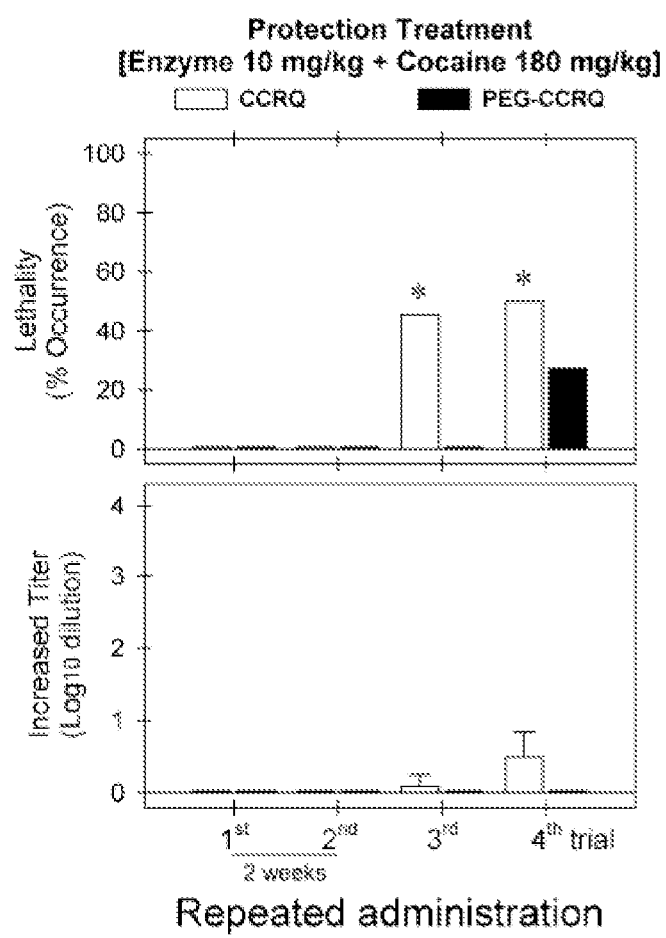
FIG. 20 shows the effectiveness of CCRQ and PEG-CCRQ in preventing cocaine-induced toxicity in mice following repeated administration.
Figure 21:
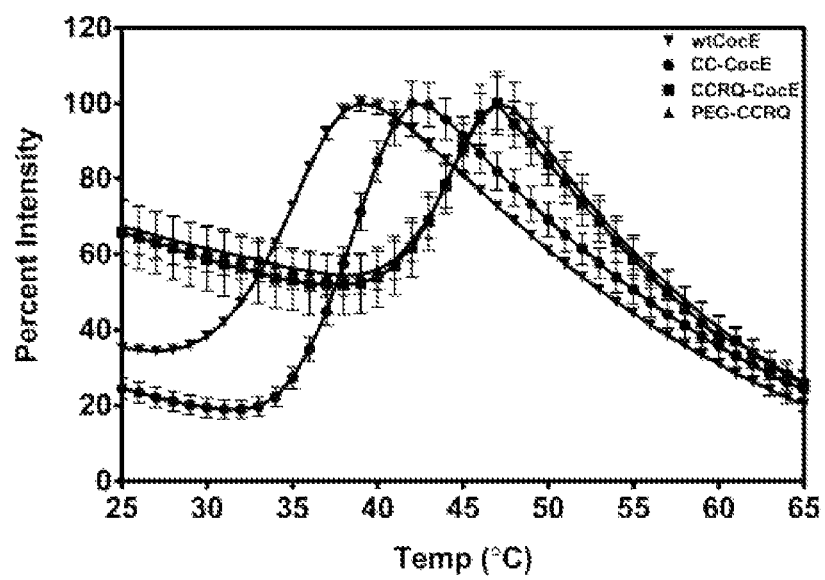
FIG. 21 shows activity of WT and mutant CocE at various temperatures.
Figure 22:
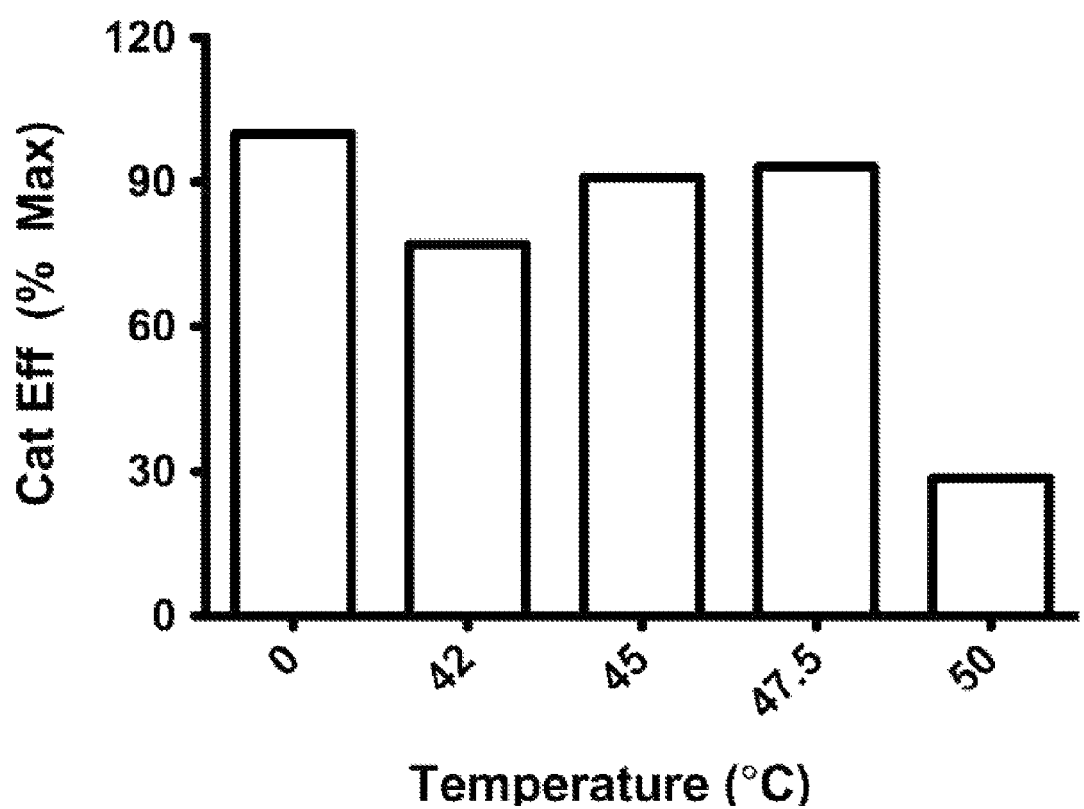
FIG. 22 shows catalytic activity of WT and mutant CocE at various temperatures.

Measurement of immune response to PEG-CCRQ: PEGylation of proteins or peptides have been shown to reduce immunogenicity of foreign proteins (Caliceti and Veronese, (2003) *Advanced Drug Delivery Reviews* 55, 1261-1277). To determine if PEG-CCRQ elicited an immune response in mice and thereby lost its effectiveness after repeated exposure (FIG. 20), CCRQ (open bars) or PEG-CCRQ (dark bars) was administered at a 10 mg/kg dose once every two weeks four times and at every time point anti-enzyme antibody and any diminution of the effectiveness of the enzyme were measured. Effectiveness of the enzyme in protecting mice against lethal doses of cocaine was measured using the standard lethality assay. As seen in the bar graph (FIG. 20, bottom panel) only after fourth exposure with CCRQ, was an approximately a 1000-fold increase in anti-CocE antibodies and no increase in antibody titer with PEG-CCRQ administration at this time point observed. As shown in the top panel, CCRQ loses its effectiveness after the third and the fourth injections, where it fails to protect 40% (3rd exposure) and approximately 50% (4th exposure) of the animals from lethal dose of cocaine (180 mg/kg). After the fourth exposure PEG-CCRQ failed to protect 25% of the animals even though anti-CocE antibody titer at this stage was negligible.

TABLE 1

Kinetic behavior of CocE variants.
The metabolism of cocaine by purified preparations of CC-CocE, CCRQ-CocE or PEG-CCRQ-CocE was measured as described in Materials and Methods Section.

| CocE variant | $K_{cat}$ (s$^{-1}$) | $K_m$ (mM) | $K_{cat}/K_m$ (s$^{-1}$ M$^{-1}$) |
|---|---|---|---|
| CC-CocE | 49.99 ± 4.66 | 0.0212 ± 0.004 | 2.37 × 10$^6$ ± 0.22 × 10$^6$ |
| CCRQ-CocE | 56.68 ± 4.90 | 0.0266 ± 0.001 | 2.12 × 10$^6$ ± 0.88 × 10$^6$ |

TABLE 1-continued

Kinetic behavior of CocE variants.
The metabolism of cocaine by purified preparations of CC-CocE, CCRQ-CocE or PEG-CCRQ-CocE was measured as described in Materials and Methods Section.

| CocE variant | $K_{cat}$ (s$^{-1}$) | $K_m$ (mM) | $K_{cat}/K_m$ (s$^{-1}$ M$^{-1}$) |
|---|---|---|---|
| PEG-CCRQ-CocE | 40.06 ± 3.24 | 0.0190 ± 0.002 | 2.11 × 10$^6$ ± 0.10 × 10$^6$ |

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

---

We claim:

1. A composition comprising a mutant cocaine esterase (CocE) polypeptide, wherein said cocaine esterase polypeptide has at least one mutation selected from the group consisting of G4C and S10C relative to the CocE polypeptide of SEQ ID NO:1 at the dimer interface, and wherein said mutation stabilizes the dimer interface between monomers of said CocE.

2. The composition of claim 1, wherein said mutant CocE polypeptide has an increased half life relative to wild type CocE.

3. The composition of claim 2, wherein said half life is at least 1 hour.

4. The composition of claim 2, wherein said half life is at least 1 day.

5. The composition of claim 2, wherein said half life is at least 3 days.

6. The composition of claim 1, wherein said mutant CocE polypeptide has G4C and S10C mutations relative to the CocE polypeptide of SEQ ID NO:1.

7. The composition of claim 1, wherein said mutant CocE polypeptide further comprises as least one additional mutation that stabilizes inter-domain or intra-domain contacts in domain II of said polypeptide.

8. The composition of claim 7, wherein said additional mutation is selected from the group consisting of T172R, G173Q and L169K relative to the CocE polypeptide of SEQ ID NO:1.

9. The composition of claim 8, wherein said additional mutation is selected from the group consisting of T172R+G172Q and L169K+G173Q relative to the CocE polypeptide of SEQ ID NO:1.

10. The composition of claim 8, wherein said mutant CocE polypeptide has G4C, S10C, L169K and G173Q mutations relative to the CocE polypeptide of SEQ ID NO:1.

11. The composition of claim 8, wherein said mutant CocE polypeptide has G4C, S10C, T172R and G173Q mutations relative to the CocE polypeptide of SEQ ID NO:1.

12. The composition of claim 1, wherein said mutant CocE polypeptide is PEGylated.

13. The composition of claim 12, wherein said CocE mutant polypeptide has A92C and S99C mutations relative to the CocE polypeptide further of SEQ ID NO:1.

14. The composition of claim 13, wherein said CocE mutant polypeptide further has C429S and C477S mutations relative to the CocE polypeptide of SEQ ID NO:1.

15. A method of reducing at least one biological activity of cocaine, comprising: administering a pharmaceutical composition comprising a mutant cocaine esterase (CocE) polypeptide, wherein said cocaine esterase polypeptide has at least one mutation at the dimer interface selected from the group consisting of G4C and S10C relative to the CocE polypeptide of SEQ ID NO:1, and wherein said mutation stabilizes the dimer interface between monomers of said CocE to a subject that has previously ingested cocaine or is likely to ingest cocaine.

16. The method of claim 15, wherein said subject is addicted to cocaine.

17. The method of claim 15, wherein said subject has ingested an overdose of cocaine.

18. The method of claim 15, wherein said pharmaceutical composition is administered once.

19. The method of claim 15, wherein said pharmaceutical composition is administered more than once.

20. A composition comprising a nucleic acid encoding a mutant cocaine esterase (CocE) polypeptide, wherein said cocaine esterase polypeptide has at least one mutation at the dimer interface selected from the group consisting of G4C and S10C relative to the CocE polypeptide of SEQ ID NO:1, and wherein said mutation stabilizes the dimer interface between monomers of said CocE.

21. The composition of claim 20, wherein said nucleic acid sequence is selected from the group consisting of SEQ ID NOs: 12 and 14.

* * * * *

UNITED STATES PATENT AND TRADEMARK OFFICE
CERTIFICATE OF CORRECTION

PATENT NO.         : 8,501,692 B2                                    Page 1 of 1
APPLICATION NO.    : 13/515511
DATED              : August 6, 2013
INVENTOR(S)        : Sunahara et al.

It is certified that error appears in the above-identified patent and that said Letters Patent is hereby corrected as shown below:

Title Page, correct Item (75) Inventors, to read:

-- Roger K. Sunahara, Ann Arbor, MI US;
John J.G. Tesmer, Ann Arbor, MI US;
Diwahar Narasimhan, Ypsilanti, MI US;
James H. Woods, Ann Arbor, MI US;
Mark R. Nance, Ann Arbor, MI US;
Elin Edwald, Ann Arbor, MI US; and
Donald Landry, New York, NY US. --.

Signed and Sealed this
Thirteenth Day of January, 2015

Michelle K. Lee
*Deputy Director of the United States Patent and Trademark Office*

SEQUENCE LISTING

```
<160> NUMBER OF SEQ ID NOS: 26

<210> SEQ ID NO 1
<211> LENGTH: 574
<212> TYPE: PRT
<213> ORGANISM: Rhodococcus

<400> SEQUENCE: 1

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
    210                 215                 220
```

```
Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
            245                 250                 255

Trp Tyr Asp Gly Phe Val Gly Glu Ser Leu Arg Thr Phe Val Ala Val
        260                 265                 270

Lys Asp Asn Ala Asp Ala Arg Leu Val Val Gly Pro Trp Ser His Ser
    275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
        340                 345                 350

Leu Pro Asp Thr Ala Tyr Thr Pro Phe Tyr Leu Gly Ser Gly Ala
    355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Val Leu Cys Tyr Ser Thr
        420                 425                 430

Glu Val Leu Thr Asp Pro Val Glu Val Thr Gly Thr Val Ser Ala Arg
    435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
        500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 2
<211> LENGTH: 587
<212> TYPE: PRT
<213> ORGANISM: Rhodococcus

<400> SEQUENCE: 2

Met Val Asp Cys Asn Tyr Ser Val Ala Cys Asn Val Met Val Pro Met
1               5                   10                  15

Arg Asp Gly Val Arg Leu Ala Val Asp Leu Tyr Arg Pro Asp Ala Asp
            20                  25                  30
```

Gly Pro Val Pro Val Leu Leu Val Arg Asn Pro Tyr Asp Lys Phe Asp
         35                  40                  45

Val Phe Ala Trp Ser Thr Gln Ser Thr Asn Trp Leu Glu Phe Val Arg
 50                  55                  60

Asp Gly Tyr Ala Val Val Ile Gln Asp Thr Arg Gly Leu Phe Ala Ser
 65                  70                  75                  80

Glu Gly Glu Phe Val Pro His Val Asp Asp Glu Ala Asp Ala Glu Asp
                     85                  90                  95

Thr Leu Ser Trp Ile Leu Glu Gln Ala Trp Cys Asp Gly Asn Val Gly
                 100                 105                 110

Met Phe Gly Val Ser Tyr Leu Gly Val Thr Gln Trp Gln Ala Ala Val
             115                 120                 125

Ser Gly Val Gly Gly Leu Lys Ala Ile Ala Pro Ser Met Ala Ser Ala
         130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                 165                 170                 175

Ser Arg Ser Asp Ala Arg Pro Glu Asp Ala Ala Asp Phe Val Gln Leu
             180                 185                 190

Ala Ala Ile Leu Asn Asp Val Ala Gly Ala Ala Ser Val Thr Pro Leu
         195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                 245                 250                 255

Trp Tyr Asp Gly Phe Val Gly Glu Ser Leu Arg Thr Phe Val Ala Val
             260                 265                 270

Lys Asp Asn Ala Asp Ala Arg Leu Val Val Gly Pro Trp Ser His Ser
         275                 280                 285

Asn Leu Thr Gly Arg Asn Ala Asp Arg Lys Phe Gly Ile Ala Ala Thr
     290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                 325                 330                 335

Leu Phe Val Met Gly Ile Asp Glu Trp Arg Asp Glu Thr Asp Trp Pro
             340                 345                 350

Leu Pro Asp Thr Ala Tyr Thr Pro Phe Tyr Leu Gly Ser Gly Ala
         355                 360                 365

Ala Asn Thr Ser Thr Gly Gly Gly Thr Leu Ser Thr Ser Ile Ser Gly
     370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                 405                 410                 415

Asp Gln Arg Pro Ile His Asp Arg Asp Val Leu Cys Tyr Ser Thr
             420                 425                 430

Glu Val Leu Thr Asp Pro Val Glu Val Thr Gly Thr Val Ser Ala Arg
         435                 440                 445

Leu Phe Val Ser Ser Ser Ala Val Asp Thr Asp Phe Thr Ala Lys Leu
     450                 455                 460

-continued

```
Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His His
            580                 585

<210> SEQ ID NO 3
<211> LENGTH: 587
<212> TYPE: PRT
<213> ORGANISM: Rhodococcus

<400> SEQUENCE: 3

Met Val Asp Cys Asn Tyr Ser Val Ala Cys Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255
```

```
Trp Tyr Asp Gly Phe Val Gly Glu Ser Leu Arg Thr Phe Val Ala Val
                260                 265                 270
Lys Asp Asn Ala Asp Ala Arg Leu Val Val Gly Pro Trp Ser His Ser
            275                 280                 285
Asn Leu Thr Gly Arg Asn Cys Asp Arg Lys Phe Gly Ile Ala Ala Thr
        290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
            340                 345                 350
Leu Pro Asp Thr Ala Tyr Thr Pro Phe Tyr Leu Gly Ser Gly Ala
        355                 360                 365
Ala Asn Thr Ser Thr Gly Gly Thr Leu Ser Thr Ser Ile Ser Gly
        370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Val Leu Cys Tyr Ser Thr
            420                 425                 430
Glu Val Leu Thr Asp Pro Val Glu Val Thr Gly Thr Val Ser Ala Arg
        435                 440                 445
Leu Phe Val Ser Ser Ala Val Asp Thr Asp Phe Thr Ala Lys Leu
        450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
            500                 505                 510
Val Phe Leu Pro Gly His Arg Ile Met Val Gln Val Ser Ser Ser Asn
        515                 520                 525
Phe Pro Lys Tyr Asp Arg Asn Ser Asn Thr Gly Gly Val Ile Ala Arg
        530                 535                 540
Glu Gln Leu Glu Glu Met Cys Thr Ala Val Asn Arg Ile His Arg Gly
545                 550                 555                 560
Pro Glu His Pro Ser His Ile Val Leu Pro Ile Ile Lys Arg Lys Leu
                565                 570                 575
Ala Ala Ala Leu Glu His His His His His
            580                 585

<210> SEQ ID NO 4
<211> LENGTH: 587
<212> TYPE: PRT
<213> ORGANISM: Rhodococcus

<400> SEQUENCE: 4

Met Val Asp Cys Asn Tyr Ser Val Ala Cys Asn Val Met Val Pro Met
1               5                   10                  15
Arg Asp Gly Val Arg Leu Ala Val Asp Leu Tyr Arg Pro Asp Ala Asp
                20                  25                  30
Gly Pro Val Pro Val Leu Leu Val Arg Asn Pro Tyr Asp Lys Phe Asp
            35                  40                  45
```

Val Phe Ala Trp Ser Thr Gln Ser Thr Asn Trp Leu Glu Phe Val Arg
 50                   55                  60

Asp Gly Tyr Ala Val Val Ile Gln Asp Thr Arg Gly Leu Phe Ala Ser
 65                   70                  75                  80

Glu Gly Glu Phe Val Pro His Val Asp Asp Glu Ala Asp Ala Glu Asp
                 85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
                130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Arg Gln Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
                195                 200                 205

Ala Glu Gln Pro Leu Leu Gly Arg Leu Ile Pro Trp Val Ile Asp Gln
                210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
                275                 280                 285

Asn Leu Thr Gly Arg Asn Ala Asp Arg Lys Phe Gly Ile Ala Ala Thr
                290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
                355                 360                 365

Ala Asn Thr Ser Thr Gly Gly Gly Thr Leu Ser Thr Ser Ile Ser Gly
                370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
                450                 455                 460

Val Asp Val Phe Pro Asp Gly Arg Ala Ile Ala Leu Cys Asp Gly Ile
465                 470                 475                 480

```
Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
        500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His His
            580                 585

<210> SEQ ID NO 5
<211> LENGTH: 587
<212> TYPE: PRT
<213> ORGANISM: Rhodococcus

<400> SEQUENCE: 5

Met Val Asp Cys Asn Tyr Ser Val Ala Cys Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Lys Ile Gly Thr Gln Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270
```

-continued

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His
            580                 585

<210> SEQ ID NO 6
<211> LENGTH: 574
<212> TYPE: PRT
<213> ORGANISM: Rhodococcus

<400> SEQUENCE: 6

Met Val Asp Cys Asn Tyr Ser Val Ala Cys Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

```
Asp Gly Tyr Ala Val Val Ile Gln Asp Thr Arg Gly Leu Phe Ala Ser
 65                  70                  75                  80

Glu Gly Glu Phe Val Pro His Val Asp Glu Ala Asp Ala Glu Asp
             85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495
```

```
Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 7
<211> LENGTH: 574
<212> TYPE: PRT
<213> ORGANISM: Rhodococcus

<400> SEQUENCE: 7

Met Val Asp Cys Asn Tyr Ser Val Ala Cys Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
            85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
            165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
            210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
            245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
            275                 280                 285

Asn Leu Thr Gly Arg Asn Cys Asp Arg Lys Phe Gly Ile Ala Ala Thr
            290                 295                 300
```

```
Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
        340                 345                 350

Leu Pro Asp Thr Ala Tyr Thr Pro Phe Tyr Leu Gly Ser Gly Ala
    355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 8
<211> LENGTH: 574
<212> TYPE: PRT
<213> ORGANISM: Rhodococcus

<400> SEQUENCE: 8

Met Val Asp Cys Asn Tyr Ser Val Ala Cys Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110
```

-continued

```
Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Arg Gln Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
530                 535                 540
```

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 9
<211> LENGTH: 574
<212> TYPE: PRT
<213> ORGANISM: Rhodococcus

<400> SEQUENCE: 9

Met Val Asp Cys Asn Tyr Ser Val Ala Cys Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Lys Ile Gly Thr Gln Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

-continued

```
Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 10
<211> LENGTH: 1725
<212> TYPE: DNA
<213> ORGANISM: Rhodococcus

<400> SEQUENCE: 10
atggtggact gcaattacag tgttgcctgt aacgtgatgg ttccgatgcg tgatggggtg      60
cgtctggcgg tcgacctgta ccgaccagat gctgatggac ctgttccggt cctgctggtt     120
cgcaacccat acgacaagtt cgacgtgttc gcgtggtcga cgcagtcgac aaactggctt     180
gagttcgtgc gtgatggcta tgccgtggtc attcaagaca cgcgtggctt gttcgcatcg     240
gaaggtgagt tcgtcccgca cgttgacgac gaagctgacg ccgaggatac gttgagctgg     300
attctggaac aagcgtggtg cgacggcaat gtgggcatgt tcggcgtttc gtacttgggt     360
gtgacccagt ggcaggccgc cgtatccggc gttggtgggc tgaaggcgat cgcgccgtcc     420
atggcgtcgg cggacttgta ccgcgccccg tggtacggcc tggtggtgc gctttcagtc     480 gaggcgctgt tgggctggtc agctctcata ggtactgggc tcatcacgtc gaggtctgac     540
gccccggccg aagacgcagc cgacttcgtc caactcgcag caattctcaa tgacgtcgct     600
ggcgcggcgt cggtcacgcc cctggccgag caaccgcttc tgggccgact gattccgtgg     660
gtgatcgatc aggttgtcga tcaccccgac aacgatgaat catggcagtc cattagcttg     720
tttgaacgac tcggcgggtt ggcaacaccg gccttgatca cggctgggtg gtacgacggg     780
ttcgtcggcg aatcgttgcg cactttcgtt gcgtcaagg acaatgccga cgcacgtttg     840
gttgtcggcc cttggagtca cagcaacctc actggtcgga atgcggaccg gaagttcggc     900
```

-continued

| | |
|---|---|
| attgccgcga cctacccgat tcaagaagcc accacgatgc acaaggcatt cttcgaccgg | 960 |
| cacctccgcg gcgagaccga tgcactcgca ggcgtcccca aagtgcggct gttcgtaatg | 1020 |
| ggcatcgatg agtggcgtga cgaaacggac tggccactgc cggacacggc gtatacgccc | 1080 |
| ttctatcttg gaggtagcgg ggctgcgaat acctccacgg gtggtggaac actgtcgacg | 1140 |
| tcgatttccg gaactgaatc tgctgacacc tacctgtatg atccggccga tcccgtgcct | 1200 |
| tcgctcgggg gacgctgct gttccacaac ggagacaacg gacccgccga ccaacgtccc | 1260 |
| attcatgacc gggacgacgt gttgtgttac agcactgagg tattgaccga cccggtggaa | 1320 |
| gtaaccggca ccgtctccgc ccggctgttc gtgtcgtcat cagcggtgga cactgatttc | 1380 |
| accgccaaac ttgtcgacgt atttcccgac ggtcgcgcga tcgcgctgtg tgacgggatc | 1440 |
| gtgcggatgc ggtaccgcga gacgttggtc aatccaacct tgatcgaagc gggcgaaatc | 1500 |
| tacgaggttg ctatcgacat gcttgcaacc tcgaatgtat tcctgccagg gcatcgcatc | 1560 |
| atggtccaag tatcaagtag caacttcccg aaatacgacc gcaattcgaa taccggcgga | 1620 |
| gtaatcgcac gggaacagct cgaagagatg tgcaccgccg tgaaccgcat tcaccgagga | 1680 |
| cctgagcatc ccagccacat tgtgctgccg attatcaagc gatga | 1725 |

<210> SEQ ID NO 11
<211> LENGTH: 1764
<212> TYPE: DNA
<213> ORGANISM: Rhodococcus

<400> SEQUENCE: 11

| | |
|---|---|
| atggtggact gcaattacag tgttgcctgt aacgtgatgg ttccgatgcg tgatggggtg | 60 |
| cgtctggcgg tcgacctgta ccgaccagat gctgatggac ctgttccggt cctgctggtt | 120 |
| cgcaacccat acgacaagtt cgacgtgttc gcgtggtcga cgcagtcgac aaactggctt | 180 |
| gagttcgtgc gtgatggcta tgccgtggtc attcaagaca cgcgtggctt gttcgcatcg | 240 |
| gaaggtgagt tcgtcccgca cgttgacgac gaagctgacg ccgaggatac gttgagctgg | 300 |
| attctggaac aagcgtggtg cgacggcaat gtgggcatgt tcggcgtttc gtacttgggt | 360 |
| gtgacccagt ggcaggccgc cgtatccggc gttggtgggc tgaaggcgat cgcgccgtcc | 420 |
| atggcgtcgg cggacttgta ccgcgccccg tggtacggcc ctggtggtgc gctttcagtc | 480 |
| gaggcgctgt tgggctggtc agctctcata ggtactgggc tcatcacgtc gaggtctgac | 540 |
| gcccggcccg aagacgcagc cgacttcgtc caactcgcag caattctcaa tgacgtcgct | 600 |
| ggcgcggcgt cggtcacgcc cctggccgag caaccgcttc tgggccgact gattccgtgg | 660 |
| gtgatcgatc aggttgtcga tcaccccgac aacgatgaat catggcagtc cattagcttg | 720 |
| tttgaacgac tcgcgggtt ggcaacaccg gccttgatca cggctgggtg gtacgacggg | 780 |
| ttcgtcggcg aatcgttgcg cactttcgtt gcggtcaagg acaatgccga cgcacgtttg | 840 |
| gttgtcggcc cttggagtca cagcaacctc actggtcgga atgcggaccg gaagttcggc | 900 |
| attgccgcga cctacccgat tcaagaagcc accacgatgc acaaggcatt cttcgaccgg | 960 |
| cacctccgcg gcgagaccga tgcactcgca ggcgtcccca aagtgcggct gttcgtaatg | 1020 |
| ggcatcgatg agtggcgtga cgaaacggac tggccactgc cggacacggc gtatacgccc | 1080 |
| ttctatcttg gaggtagcgg ggctgcgaat acctccacgg gtggtggaac actgtcgacg | 1140 |
| tcgatttccg gaactgaatc tgctgacacc tacctgtatg atccggccga tcccgtgcct | 1200 |
| tcgctcgggg gacgctgct gttccacaac ggagacaacg gacccgccga ccaacgtccc | 1260 |
| attcatgacc gggacgacgt gttgtgttac agcactgagg tattgaccga cccggtggaa | 1320 |

```
gtaaccggca ccgtctccgc ccggctgttc gtgtcgtcat cagcggtgga cactgatttc    1380
accgccaaac ttgtcgacgt atttcccgac ggtcgcgcga tcgcgctgtg tgacgggatc    1440
gtgcggatgc ggtaccgcga gacgttggtc aatccaacct tgatcgaagc gggcgaaatc    1500
tacgaggttg ctatcgacat gcttgcaacc tcgaatgtat tcctgccagg gcatcgcatc    1560
atggtccaag tatcaagtag caacttcccg aaatacgacc gcaattcgaa taccggcgga    1620
gtaatcgcac gggaacagct cgaagagatg tgcaccgccg tgaaccgcat tcaccgagga    1680
cctgagcatc ccagccacat tgtgctgccg attatcaagc gaaagcttgc ggccgcactc    1740
gagcaccacc accaccacca ctga                                           1764

<210> SEQ ID NO 12
<211> LENGTH: 1725
<212> TYPE: DNA
<213> ORGANISM: Rhodococcus

<400> SEQUENCE: 12
atggtggact gcaattacag tgttgcctgt aacgtgatgg ttccgatgcg tgatggggtg     60
cgtctggcgg tcgacctgta ccgaccagat gctgatggac ctgttccggt cctgctggtt    120
cgcaacccat acgacaagtt cgacgtgttc gcgtggtcga cgcagtcgac aaactggctt    180
gagttcgtgc gtgatggcta tgccgtggtc attcaagaca cgcgtggctt gttcgcatcg    240
gaaggtgagt tcgtcccgca cgttgacgac gaagctgacg ccgaggatac gttgagctgg    300
attctggaac aagcgtggtg cgacggcaat gtgggcatgt tcggcgtttc gtacttgggt    360
gtgacccagt ggcaggccgc cgtatccggc gttggtgggc tgaaggcgat cgcgccgtcc    420
atggcgtcgg cggacttgta ccgcgccccg tggtacggcc ctggtggtgc gctttcagtc    480
gaggcgctgt tgggctggtc agctctcata ggtcgccagc tcatcacgtc gaggtctgac    540
gcccggcccg aagacgcagc cgacttcgtc caactcgcag caattctcaa tgacgtcgct    600
ggcgcggcgt cggtcacgcc cctggccgag caaccgcttc tgggccgact gattccgtgg    660
gtgatcgatc aggttgtcga tcaccccgac aacgatgaat catggcagtc cattagcttg    720
tttgaacgac tcggcgggtt ggcaacaccg gccttgatca cggctgggtg gtacgacggg    780
ttcgtcggcg aatcgttgcg cactttcgtt gcggtcaagg acaatgccga cgcacgtttg    840
gttgtcggcc cttggagtca cagcaaccct actggtcgga atgcggaccg gaagttcggc    900
attgccgcga cctacccgat tcaagaagcc accacgatgc acaaggcatt cttcgaccgg    960
cacctccgcg gcgagaccga tgcactcgca ggcgtcccca agtgcggct gttcgtaatg   1020 ggcatcgatg agtggcgtga cgaaacggac tggccactgc cggacacggc gtatacgccc   1080
ttctatcttg gaggtagcgg ggctgcgaat acctccacgg tggtggaac actgtcgacg    1140 tcgatttccg gaactgaatc tgctgacacc tacctgtatg atccggccga tcccgtgcct   1200
tcgctcgggg ggacgctgct gttccacaac ggagacaacg acccgccga ccaacgtccc    1260 attcatgacc gggacgacgt gttgtgttac agcactgagg tattgaccga cccggtggaa   1320
gtaaccggca ccgtctccgc ccggctgttc gtgtcgtcat cagcggtgga cactgatttc    1380
accgccaaac ttgtcgacgt atttcccgac ggtcgcgcga tcgcgctgtg tgacgggatc    1440
gtgcggatgc ggtaccgcga gacgttggtc aatccaacct tgatcgaagc gggcgaaatc    1500
tacgaggttg ctatcgacat gcttgcaacc tcgaatgtat tcctgccagg gcatcgcatc    1560
atggtccaag tatcaagtag caacttcccg aaatacgacc gcaattcgaa taccggcgga    1620
```

```
gtaatcgcac gggaacagct cgaagagatg tgcaccgccg tgaaccgcat tcaccgagga   1680
cctgagcatc ccagccacat tgtgctgccg attatcaagc gatga                  1725
```

<210> SEQ ID NO 13
<211> LENGTH: 1764
<212> TYPE: DNA
<213> ORGANISM: Rhodococcus

<400> SEQUENCE: 13

```
atggtggact gcaattacag tgttgcctgt aacgtgatgg ttccgatgcg tgatggggtg     60
cgtctggcgg tcgacctgta ccgaccagat gctgatggac ctgttccggt cctgctggtt    120
cgcaacccat acgacaagtt cgacgtgttc gcgtggtcga cgcagtcgac aaactggctt    180
gagttcgtgc gtgatggcta tgccgtggtc attcaagaca cgcgtggctt gttcgcatcg    240
gaaggtgagt tcgtcccgca cgttgacgac gaagctgacg ccgaggatac gttgagctgg    300
attctggaac aagcgtggtg cgacggcaat gtgggcatgt tcggcgtttc gtacttgggt    360
gtgacccagt ggcaggccgc cgtatccggc gttggtgggc tgaaggcgat cgcgccgtcc    420
atggcgtcgg cggacttgta ccgcgccccg tggtacggcc ctggtggtgc gctttcagtc    480
gaggcgctgt tgggctggtc agctctcata ggtcgccagc tcatcacgtc gaggtctgac    540
gcccggcccg aagacgcagc cgacttcgtc caactcgcag caattctcaa tgacgtcgct    600
ggcgcggcgt cggtcacgcc cctggccgag caaccgcttc tgggccgact gattccgtgg    660
gtgatcgatc aggttgtcga tcaccccgac aacgatgaat catggcagtc cattagcttg    720
tttgaacgac tcggcgggtt ggcaacaccg gccttgatca cggctgggtg gtacgacggg    780
ttcgtcggcg aatcgttgcg cactttcgtt gcggtcaagg acaatgccga cgcacgtttg    840
gttgtcggcc cttggagtca cagcaacctc actggtcgga atgcggaccg gaagttcggc    900
attgccgcga cctacccgat tcaagaagcc accacgatgc acaaggcatt cttcgaccgg    960
cacctccgcg gcgagaccga tgcactcgca ggcgtcccca aagtgcggct gttcgtaatg   1020
ggcatcgatg agtggcgtga cgaaacggac tggccactgc cggacacggc gtatacgccc   1080
ttctatcttg gaggtagcgg ggctgcgaat acctccacgg tggtggaaac actgtcgacg   1140
tcgatttccg gaactgaatc tgctgacacc tacctgtatg atccggccga tcccgtgcct   1200
tcgctcgggg ggacgctgct gttccacaac ggagacaacg gacccgccga ccaacgtccc   1260
attcatgacc gggacgacgt gttgtgttac agcactgagg tattgaccga cccggtggaa   1320
gtaaccggca ccgtctccgc ccggctgttc gtgtcgtcat cagcggtgga cactgatttc   1380
accgccaaac ttgtcgacgt atttcccgac ggtcgcgcga tcgcgctgtg tgacgggatc   1440
gtgcggatgc ggtaccgcga gacgttggtc aatccaacct tgatcgaagc gggcgaaatc   1500
tacgaggttg ctatcgacat gcttgcaacc tcgaatgtat tcctgccagg catcgcatc    1560 atggtccaag tatcaagtag caacttcccg aaatacgacc gcaattcgaa taccggcgga   1620
gtaatcgcac gggaacagct cgaagagatg tgcaccgccg tgaaccgcat tcaccgagga   1680
cctgagcatc ccagccacat tgtgctgccg attatcaagc gaaagcttgc ggccgcactc   1740
gagcaccacc accaccacca ctga                                          1764
```

<210> SEQ ID NO 14
<211> LENGTH: 1725
<212> TYPE: DNA
<213> ORGANISM: Rhodococcus

```
<400> SEQUENCE: 14
atggtggact gcaattacag tgttgcctgt aacgtgatgg ttccgatgcg tgatggggtg      60
cgtctggcgg tcgacctgta ccgaccagat gctgatggac ctgttccggt cctgctggtt    120
cgcaacccat acgacaagtt cgacgtgttc gcgtggtcga cgcagtcgac aaactggctt    180
gagttcgtgc gtgatggcta tgccgtggtc attcaagaca cgcgtggctt gttcgcatcg    240
gaaggtgagt tcgtcccgca cgttgacgac gaagctgacg ccgaggatac gttgagctgg    300
attctggaac aagcgtggtg cgacggcaat gtgggcatgt tcggcgtttc gtacttgggt    360
gtgacccagt ggcaggccgc cgtatccggc gttggtgggc tgaaggcgat cgcgccgtcc    420
atggcgtcgg cggacttgta ccgcgccccg tggtacggcc ctggtggtgc gctttcagtc    480
gaggcgctgt tgggctggtc agctaagata ggtactcagc tcatcacgtc gaggtctgac    540
gcccggcccg aagacgcagc cgacttcgtc caactcgcag caattctcaa tgacgtcgct    600
ggcgcggcgt cggtcacgcc cctggccgag caaccgcttc tgggccgact gattccgtgg    660
gtgatcgatc aggttgtcga tcaccccgac aacgatgaat catggcagtc cattagcttg    720
tttgaacgac tcgcgggtt ggcaacaccg gccttgatca cggctgggtg gtacgacggg    780
ttcgtcggcg aatcgttgcg cactttcgtt gcggtcaagg acaatgccga cgcacgtttg    840
gttgtcggcc cttggagtca cagcaacctc actggtcgga atgcggaccg gaagttcggc    900
attgccgcga cctacccgat tcaagaagcc accacgatgc acaaggcatt cttcgaccgg    960
cacctccgcg gcgagaccga tgcactcgca ggcgtcccca aagtgcggct gttcgtaatg   1020
ggcatcgatg agtggcgtga cgaaacggac tggccactgc cggacacggc gtatacgccc   1080
ttctatcttg gaggtagcgg ggctgcgaat acctccacgg gtggtggaac actgtcgacg   1140
tcgatttccg gaactgaatc tgctgacacc tacctgtatg atccggccga tcccgtgcct   1200
tcgctcgggg gacgctgct gttccacaac ggagacaacg acccgccga ccaacgtccc   1260 attcatgacc gggacgacgt gttgtgttac agcactgagg tattgaccga cccggtggaa   1320
gtaaccggca ccgtctccgc ccggctgttc gtgtcgtcat cagcggtgga cactgatttc   1380
accgccaaac ttgtcgacgt atttcccgac ggtcgcgcga tcgcgctgtg tgacgggatc   1440
gtgcggatgc ggtaccgcga gacgttggtc aatccaacct tgatcgaagc gggcgaaatc   1500
tacgaggttg ctatcgacat gcttgcaacc tcgaatgtat tcctgccagg gcatcgcatc   1560
atggtccaag tatcaagtag caacttcccg aaatacgacc gcaattcgaa taccggcgga   1620
gtaatcgcac gggaacagct cgaagagatg tgcaccgccg tgaaccgcat tcaccgagga   1680
cctgagcatc ccagccacat tgtgctgccg attatcaagc gatga                   1725

<210> SEQ ID NO 15
<211> LENGTH: 1764
<212> TYPE: DNA
<213> ORGANISM: Rhodococcus

<400> SEQUENCE: 15
atggtggact gcaattacag tgttgcctgt aacgtgatgg ttccgatgcg tgatggggtg      60
cgtctggcgg tcgacctgta ccgaccagat gctgatggac ctgttccggt cctgctggtt    120
cgcaacccat acgacaagtt cgacgtgttc gcgtggtcga cgcagtcgac aaactggctt    180
gagttcgtgc gtgatggcta tgccgtggtc attcaagaca cgcgtggctt gttcgcatcg    240
gaaggtgagt tcgtcccgca cgttgacgac gaagctgacg ccgaggatac gttgagctgg    300
attctggaac aagcgtggtg cgacggcaat gtgggcatgt tcggcgtttc gtacttgggt    360
```

-continued

```
gtgacccagt ggcaggccgc cgtatccggc gttggtgggc tgaaggcgat cgcgccgtcc      420
atggcgtcgg cggacttgta ccgcgccccg tggtacggcc ctggtggtgc gctttcagtc      480
gaggcgctgt tgggctggtc agctaagata ggtactcagc tcatcacgtc gaggtctgac      540
gcccggcccg aagacgcagc cgacttcgtc caactcgcag caattctcaa tgacgtcgct      600
ggcgcggcgt cggtcacgcc cctggccgag caaccgcttc tgggccgact gattccgtgg      660
gtgatcgatc aggttgtcga tcaccccgac aacgatgaat catggcagtc cattagcttg      720
tttgaacgac tcggcgggtt ggcaacaccg gccttgatca cggctgggtg gtacgacggg      780
ttcgtcggcg aatcgttgcg cactttcgtt gcggtcaagg acaatgccga cgcacgtttg      840
gttgtcggcc cttggagtca cagcaacctc actggtcgga atgcggaccg gaagttcggc      900
attgccgcga cctacccgat tcaagaagcc accacgatgc acaaggcatt cttcgaccgg      960
cacctccgcg gcgagaccga tgcactcgca ggcgtcccca aagtgcggct gttcgtaatg     1020
ggcatcgatg agtggcgtga cgaaacggac tggccactgc cggacacggc gtatacgccc     1080
ttctatcttg gaggtagcgg ggctgcgaat acctccacgg gtggtggaac actgtcgacg     1140
tcgatttccg gaactgaatc tgctgacacc tacctgtatg atccggccga tcccgtgcct     1200
tcgctcgggg ggacgctgct gttccacaac ggagacaacg gacccgccga ccaacgtccc     1260
attcatgacc gggacgacgt gttgtgttac agcactgagg tattgaccga cccggtggaa     1320
gtaaccggca ccgtctccgc ccggctgttc gtgtcgtcat cagcggtgga cactgatttc     1380
accgccaaac ttgtcgacgt atttcccgac ggtcgcgcga tcgcgctgtg tgacgggatc     1440
gtgcggatgc ggtaccgcga gacgttggtc aatccaacct tgatcgaagc gggcgaaatc     1500
tacgaggttg ctatcgacat gcttgcaacc tcgaatgtat tcctgccagg gcatcgcatc     1560
atggtccaag tatcaagtag caacttcccg aaatacgacc gcaattcgaa taccggcgga     1620
gtaatcgcac gggaacagct cgaagagatg tgcaccgccg tgaaccgcat tcaccgagga     1680
cctgagcatc ccagccacat tgtgctgccg attatcaagc gaaagcttgc ggccgcactc     1740
gagcaccacc accaccacca ctga                                            1764
```

<210> SEQ ID NO 16
<211> LENGTH: 587
<212> TYPE: PRT
<213> ORGANISM: Rhodococcus

<400> SEQUENCE: 16

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Cys Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125
```

```
Ser Gly Val Gly Gly Leu Lys Ala Ile Ala Pro Ser Met Ala Ser Ala
130                 135                 140
Asp Leu Tyr Arg Ala Pro Trp Tyr Gly Pro Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Arg Pro Glu Asp Ala Ala Asp Phe Val Gln Leu
            180                 185                 190
Ala Ala Ile Leu Asn Asp Val Ala Gly Ala Ser Val Thr Pro Leu
        195                 200                 205
Ala Glu Gln Pro Leu Leu Gly Arg Leu Ile Pro Trp Val Ile Asp Gln
210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
            260                 265                 270
Lys Asp Asn Ala Asp Ala Arg Leu Val Val Gly Pro Trp Ser His Ser
        275                 280                 285
Asn Leu Thr Gly Arg Asn Ala Asp Arg Lys Phe Gly Ile Ala Ala Thr
    290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
            340                 345                 350
Leu Pro Asp Thr Ala Tyr Thr Pro Phe Tyr Leu Gly Ser Gly Ala
        355                 360                 365
Ala Asn Thr Ser Thr Gly Gly Thr Leu Ser Thr Ser Ile Ser Gly
    370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Asp Val Leu Cys Tyr Ser Thr
            420                 425                 430
Glu Val Leu Thr Asp Pro Val Glu Val Thr Gly Thr Val Ser Ala Arg
        435                 440                 445
Leu Phe Val Ser Ser Ala Val Asp Thr Asp Phe Thr Ala Lys Leu
    450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
            500                 505                 510
Val Phe Leu Pro Gly His Arg Ile Met Val Gln Val Ser Ser Ser Asn
        515                 520                 525
Phe Pro Lys Tyr Asp Arg Asn Ser Asn Thr Gly Gly Val Ile Ala Arg
    530                 535                 540
Glu Gln Leu Glu Glu Met Cys Thr Ala Val Asn Arg Ile His Arg Gly
545                 550                 555                 560
```

```
Pro Glu His Pro Ser His Ile Val Leu Pro Ile Ile Lys Arg Lys Leu
                565                 570                 575
Ala Ala Ala Leu Glu His His His His His
            580                 585

<210> SEQ ID NO 17
<211> LENGTH: 587
<212> TYPE: PRT
<213> ORGANISM: Rhodococcus

<400> SEQUENCE: 17

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Glu Ala Asp Ala Glu Asp
                85                  90                  95

Thr Leu Cys Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350
```

```
Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ser Ile Ser Gly
        370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
        450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
        500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His His
        580                 585

<210> SEQ ID NO 18
<211> LENGTH: 574
<212> TYPE: PRT
<213> ORGANISM: Rhodococcus

<400> SEQUENCE: 18

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Cys Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140
```

```
Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
            165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
        210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
        290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Asp Val Leu Cys Tyr Ser Thr
        420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
        450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

<210> SEQ ID NO 19
<211> LENGTH: 574
<212> TYPE: PRT
<213> ORGANISM: Rhodococcus

<400> SEQUENCE: 19

```
Met Val Asp Gly Asn Tyr Ser Val Ala Ser Asn Val Met Val Pro Met
 1               5                  10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Cys Trp Ile Leu Glu Gln Ala Trp Cys Asp Gly Asn Val Gly
               100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
370                 375                 380
```

```
Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Val Leu Cys Tyr Ser Thr
        420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 20
<211> LENGTH: 574
<212> TYPE: PRT
<213> ORGANISM: Rhodococcus

<400> SEQUENCE: 20

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190
```

```
Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
    355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Ser Tyr Ser Thr
            420                 425                 430

Glu Val Leu Thr Asp Pro Val Glu Val Thr Gly Thr Val Ser Ala Arg
    435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Ser Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 21
<211> LENGTH: 574
<212> TYPE: PRT
<213> ORGANISM: Rhodococcus
```

<400> SEQUENCE: 21

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Cys Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415
```

-continued

```
Asp Gln Arg Pro Ile His Asp Arg Asp Asp Val Leu Ser Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Ser Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 22
<211> LENGTH: 574
<212> TYPE: PRT
<213> ORGANISM: Rhodococcus

<400> SEQUENCE: 22

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Glu Ala Asp Ala Glu Asp
                85                  90                  95

Thr Leu Cys Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
    115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
    195                 200                 205

Ala Glu Gln Pro Leu Leu Gly Arg Leu Ile Pro Trp Val Ile Asp Gln
210                 215                 220
```

```
Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
            245                 250                 255

Trp Tyr Asp Gly Phe Val Gly Glu Ser Leu Arg Thr Phe Val Ala Val
        260                 265                 270

Lys Asp Asn Ala Asp Ala Arg Leu Val Val Gly Pro Trp Ser His Ser
    275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
        340                 345                 350

Leu Pro Asp Thr Ala Tyr Thr Pro Phe Tyr Leu Gly Ser Gly Ala
    355                 360                 365

Ala Asn Thr Ser Thr Gly Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Val Leu Ser Tyr Ser Thr
        420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Ser Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
        500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 23
<211> LENGTH: 587
<212> TYPE: PRT
<213> ORGANISM: Rhodococcus

<400> SEQUENCE: 23

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30
```

```
Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
 50                  55                  60

Asp Gly Tyr Ala Val Val Ile Gln Asp Thr Arg Gly Leu Phe Ala Ser
 65                  70                  75                  80

Glu Gly Glu Phe Val Pro His Val Asp Asp Glu Ala Asp Ala Glu Asp
                    85                  90                  95

Thr Leu Ser Trp Ile Leu Glu Gln Ala Trp Cys Asp Gly Asn Val Gly
                100                 105                 110

Met Phe Gly Val Ser Tyr Leu Val Thr Gln Trp Gln Ala Ala Val
            115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
            355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Ser Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ser Ala Val Asp Thr Asp Phe Thr Ala Lys Leu
450                 455                 460
```

```
Val Asp Val Phe Pro Asp Gly Arg Ala Ile Ala Leu Ser Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
        500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His His
            580                 585

<210> SEQ ID NO 24
<211> LENGTH: 587
<212> TYPE: PRT
<213> ORGANISM: Rhodococcus

<400> SEQUENCE: 24

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Cys Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255
```

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
        290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
        370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Ser Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
        450                 455                 460

Val Asp Val Phe Pro Asp Gly Arg Ala Ile Ala Leu Ser Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
        530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His His
            580                 585

<210> SEQ ID NO 25
<211> LENGTH: 587
<212> TYPE: PRT
<213> ORGANISM: Rhodococcus

<400> SEQUENCE: 25

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

```
Val Phe Ala Trp Ser Thr Gln Ser Thr Asn Trp Leu Glu Phe Val Arg
 50                  55                  60

Asp Gly Tyr Ala Val Val Ile Gln Asp Thr Arg Gly Leu Phe Ala Ser
 65                  70                  75                  80

Glu Gly Glu Phe Val Pro His Val Asp Asp Glu Ala Asp Ala Glu Asp
                 85                  90                  95

Thr Leu Cys Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
                195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
                275                 280                 285

Asn Leu Thr Gly Arg Asn Ala Asp Arg Lys Phe Gly Ile Ala Ala Thr
                290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
                355                 360                 365

Ala Asn Thr Ser Thr Gly Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Ser Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
                450                 455                 460

Val Asp Val Phe Pro Asp Gly Arg Ala Ile Ala Leu Ser Asp Gly Ile
465                 470                 475                 480
```

-continued

```
Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His His
            580                 585
```

<210> SEQ ID NO 26
<211> LENGTH: 13
<212> TYPE: PRT
<213> ORGANISM: Artificial Sequence
<220> FEATURE:
<223> OTHER INFORMATION: Synthetic

<400> SEQUENCE: 26

```
Lys Leu Ala Ala Ala Leu Glu His His His His His His
1               5                   10
```